United States Patent
Mirica et al.

(10) Patent No.: US 11,827,653 B2
(45) Date of Patent: Nov. 28, 2023

(54) TRIDENTATE MACROCYCLIC COMPOUNDS

(71) Applicant: The Board of Trustees of the University of Illinois, Urbana, IL (US)

(72) Inventors: Liviu M. Mirica, Champaign, IL (US); Hanah Na, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 17/833,160

(22) Filed: Jun. 6, 2022

(65) Prior Publication Data
US 2023/0040709 A1 Feb. 9, 2023

Related U.S. Application Data

(60) Provisional application No. 63/215,131, filed on Jun. 25, 2021.

(51) Int. Cl.
*C07D 471/18* (2006.01)
*C07F 15/04* (2006.01)

(52) U.S. Cl.
CPC .......... *C07F 15/045* (2013.01); *C07D 471/18* (2013.01); *C07F 15/04* (2013.01)

(58) Field of Classification Search
CPC .............................. C07D 471/18; C07F 15/04
See application file for complete search history.

(56) References Cited

U.S. PATENT DOCUMENTS 9,308,526 B2  4/2016  Kim et al.

FOREIGN PATENT DOCUMENTS

| CN | 107744824 A | 3/2018 |
| CN | 109126854 B | 9/2020 |
| CN | 109261211 B | 3/2021 |

OTHER PUBLICATIONS

Maquestiau et al., "[3.2] Metacyclophanes, I. Synthèse et étude du N-cyclohexyl-2-aza [3.2] métacyclophane," Tetrahedron Lett., 11(42):3645-3648, Aug. 1970.

Na et al., "Deciphering the mechanism of the Ni-photocatalyzed C—O cross-coupling reaction using a tridentate byridinophane ligand", Nature Communications Mar. 13, 2022, 1313, 11pgs.

Rocha et al., "Sunlight-Driven Dehydrogenative Oxidation Photocatalysis by a Mononuclear Complex Acting as both Chromophore and Catalyst," J Braz Chem Soc., 31(11):2421-2429, Oct. 2020.

Shields et al., "Long-Lived Charge-Transfer States of Nickel(II) Aryl Halide Complexes Facilitate Bimolecular Photoinduced Electron Transfer," J Am Chem Soc., 140(8):3035-3039, Feb. 2018.

Sun et al., "Elucidation of a Redox-Mediated Reaction Cycle for Nickel-Catalyzed Cross Coupling," J Am Chem Soc., 141(1):89-93, Dec. 2018.

Sun et al., "General Paradigm in Photoredox Ni-Catalyzed Cross-Coupling Allows for Light-Free Access to Reactivity," Ange Chem Int Ed., 59(24):9527-9533, Jun. 2020.

Takemura et al., "A New Synthetic Method of [2.2]cyclophanes," Tetrahedron Lett., 29(9):1031-1032,1988.

Terrett et al., "Switching on Elusive Organometallic Mechanisms With Photoredox Catalysis," Nature, 524 (7565):330-334, Aug. 2015.

Visvaganesan et al., "Iron(III) Complexes of Tridentate 3N Ligands as Functional Models for Catechol Dioxygenases: The Role of Ligand N-alkyl Substitution and Solvent on Reaction Rate and Product Selectivity," Inorg Chem., 46(24):10294-10306, Oct. 2007.

Wei et al., "d7/d8 Metal Complexes Constructed from 2,6-Bis(2-benzimidazolyl)pyridyl or 2,6-Di-(pyrazol-3-yl)pyridine Derivatives: Synthesis, Structure, Characterization, and Photocatalytic Activity," ChemPlusChem, 80(3):549-558, Mar. 2015.

Wessel et al., "Improved Synthesis of Symmetrically & Asymmetrically N-Substituted Pyridinophane Derivatives," Org Biomol Chem., 15(46):9923-9931, Nov. 2017.

Yang et al., "Light-Promoted Nickel Catalysis: Etherification of Aryl Electrophiles with Alcohols Catalyzed by a Nill-Aryl Complex," Angew Chem Int Ed Engl., 59(31):12714-12719, Jul. 2020.

*Primary Examiner* — Brenda L Coleman
(74) *Attorney, Agent, or Firm* — Haukaas Fortius PLLC; Michael Haukaas

(57) ABSTRACT

Photoredox catalysis has emerged as a powerful strategy for C—O cross-coupling reactions. We herein report a new class of tridentate pyridinophane ligands $^R$N3 that allow for detailed mechanistic studies of the photocatalytic C—O coupling reaction. The derived ($^R$N3)Ni complexes are active C—O cross-coupling photocatalysts under mild conditions and without an additional photocatalyst. We also utilized the $^R$N3 ligands to study the essential but so far putative steps involving paramagnetic Ni species in a proposed catalytic cycle: the oxidative addition of an aryl bromide to a Ni(I) species, the ligand exchange at a Ni(III) center, and the C—O reductive elimination from a Ni(III) species.

20 Claims, 17 Drawing Sheets d)

e)

f)

1a g)

Bottom view of 1a

TRIDENTATE MACROCYCLIC COMPOUNDS

RELATED APPLICATIONS

This application claims priority under 35 U.S.C. § 119(e) to U.S. Provisional Patent Application No. 63/215,131, filed Jun. 25, 2021, which is incorporated herein by reference.

BACKGROUND OF THE INVENTION

The carbon-oxygen (C—O) bond-forming reactions are of particular interest in the field of organic synthesis, as C—O bonds are prevalent in many natural products, pharmaceuticals, and agrochemicals. Although Pd-based C—O cross-coupling catalysts are well established, there has been a great interest in developing sustainable alternate catalytic systems based on earth-abundant nickel. In this regard, photoredox/nickel dual catalysis and light-promoted Ni catalysis have emerged as powerful strategies for challenging C—O bond formations. Accordingly, an in-depth mechanistic understanding of Ni-mediated photocatalysis is essential for rational reaction design and optimization. From a mechanistic viewpoint, while the photocatalytic cycle is well-understood, the Ni-mediated redox cycle remains elusive as intermediates in various oxidation states (from $Ni^0$ to $Ni^{IV}$) have been proposed (Trends Chem. 2019, 1, 830). For example, the involvement of paramagnetic $Ni^I$ and $Ni^{III}$ species has been commonly implicated, yet such intermediates have not been thoroughly investigated.

Our group has employed tetradentate azamacrocycle N,N'-dialkyl-2,11-diaza[3.3](2,6)pyridinophanes ($^RN4$) ligands to isolate and characterize $Ni^{III}$ species capable of C—C and C-heteroatom bond formation reactions, and to probe involvement of different high-valent Ni species in these reactions (J. Am. Chem. Soc. 2014, 136, 6499). However, considering that the most ubiquitous ligand systems in Ni cross-coupling and photocatalysis are the bidentate bipyridine ligands, the $^RN4$ ligands are less effective owing to the crowded environment around the Ni center, which is also expected to hinder the formation of $Ni^I$ species. By contrast, a bidentate ligand structure is not suitable for stabilizing high-valent Ni species, thus hampering the investigation of such Ni intermediates.

Also, other known fac-capping tridentate N-donor ligands, such as tris(pyrazoyl)borate ($Tp^-$), tris(pyrazolyl)methane (Tpm), or 1,4,7-trimethyl-1,4,7-triazacyclononane ($Me_3TACN$) have been reported, yet they have a large degree of flexibility due to the absence of bridges between the donor atoms ($Tp^-$ or Tpm), or they are fully aliphatic macrocycles (TACN).

Accordingly, there is a need for new efficient and cost-effective catalysts to further advance the field of chemical synthesis.

SUMMARY

Considering the challenges of carbon-oxygen bond-forming reactions, we sought to identify an optimal ligand framework positioned in between bipyridine and $^RN4$ ligands in terms of denticity, molecular structure, and functionality, and thus the pyridinophane tridentate $^RN3$ ligands were targeted (Scheme 1a). These $^RN3$ ligands are structurally analogous to the $^RN4$ ligands, possessing a rigid aromatic pyridinophane framework and containing only one flexible chelating arm that allows for either a $\kappa^2$ or $\kappa^3$ coordination. Surprisingly, such $^RN3$ ligands have never been synthesized to date, likely due to the lack of an efficient synthetic route.

Scheme 1.
(a) New ligand framework design.
(b) Representative tridentate N-donor ligands commonly used for stabilizing uncommon Ni oxidation states and the newly developed trientate ligand developed in this work.

a) Tridentate ligand framework design

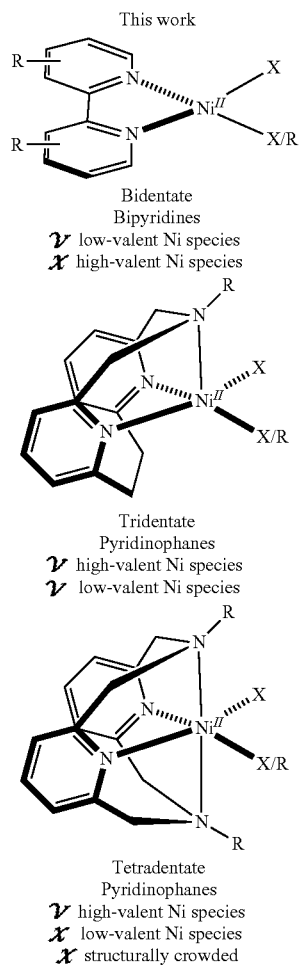

b) Examples of tridentate ligands

Commonly used tridentate ligands

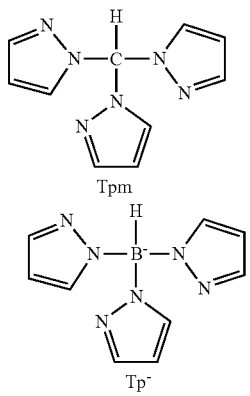

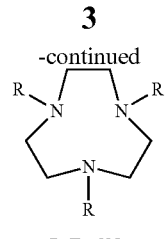

R₃TACN

This work
$^R$N3 ligands

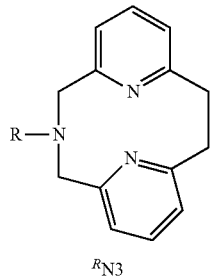

$^R$N3

In this work, we report the development of new N-alkyl-2-aza[3.2](2,6)pyridionphanes ($^R$N3, R=Me or $^i$Pr) ligands, which embody our design criteria for photocatalytic applications and mechanistic studies. The corresponding ($^R$N3)Ni complexes are active C—O cross-coupling catalysts upon light excitation and without an added precious-metal photocatalyst. Importantly, we show that the utilization of the tridentate $^R$N3 ligands allows a comprehensive examination of the Ni intermediates proposed in the individual steps of the cross-coupling catalytic cycle: oxidative addition, transmetalation/ligand exchange, and reductive elimination, all these steps involving paramagnetic $Ni^I$ or $Ni^{III}$ species.

Accordingly, this disclosure provides an organometallic compound of Formula I:

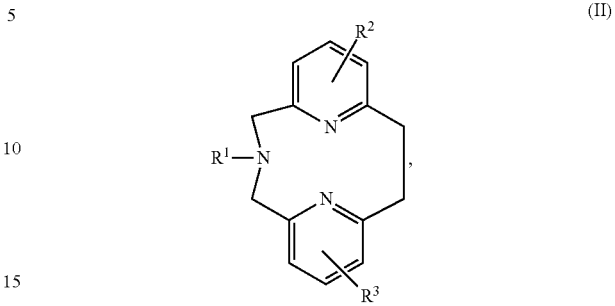

(I)

wherein

M is a transition metal;

L is a ligand and n is 1, 2, or 3;

$R^1$ is —($C_1$-$C_6$)alkyl, or —($C_3$-$C_6$)cycloalkyl; and $R^2$ and $R^3$ are each independently H, halo, —($C_1$-$C_6$)alkyl, —($C_3$-$C_6$)cycloalkyl, —O($C_1$-$C_6$)alkyl, or —N[($C_1$-$C_6$)alkyl]$_2$;

wherein each ($C_1$-$C_6$)alkyl moiety is independently unbranched or branched.

This disclosure also provides a macrocyclic compound of Formula II:

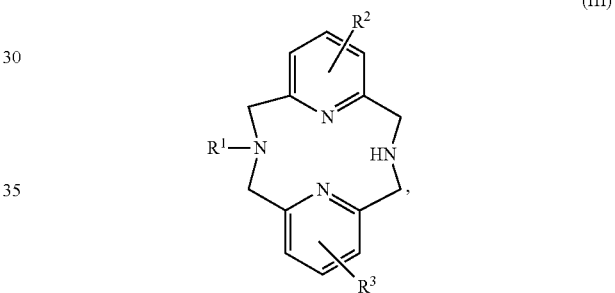

(II)

wherein $R^1$ is —($C_1$-$C_6$)alkyl, —($C_3$-$C_6$)cycloalkyl, or sulfonyl; and $R^2$ and $R^3$ are each independently H, halo, —($C_1$-$C_6$)alkyl, —($C_3$-$C_6$)cycloalkyl, —O($C_1$-$C_6$)alkyl, or —N[($C_1$-$C_6$)alkyl]$_2$;

wherein each ($C_1$-$C_6$)alkyl moiety is independently unbranched or branched.

Additionally, this disclosure provides a method for preparing a pyridinophane comprising:

a) contacting a compound of Formula III:

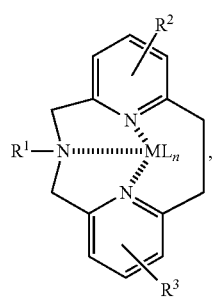

(III)

wherein $R^1$ is a nitrogen protecting group; and $R^2$ and $R^3$ are each independently H, halo, —($C_1$-$C_6$)alkyl, —($C_3$-$C_6$)cycloalkyl, —O($C_1$-$C_6$)alkyl, or —N[($C_1$-$C_6$)alkyl]$_2$; wherein each ($C_1$-$C_6$)alkyl moiety is independently unbranched or branched;

and nitrous acid to form a nitrosamine; and b) reducing the nitrosamine under suitable reaction conditions to form a pyridinophane of Formula IIB:

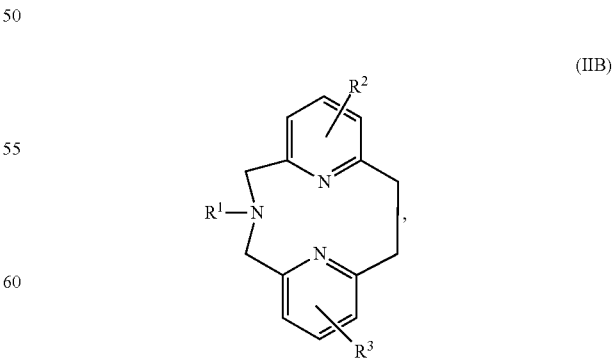

(IIB)

wherein $R^1$, $R^2$, and $R^3$ is defined for Formula III.

The invention provides novel compounds of Formulas I, II, IIB, and III intermediates for the synthesis of compounds of Formulas I, II, IIB, and III, as well as methods of preparing compounds of Formulas I, II, IIB, and III. The invention also provides compounds of Formulas I, II, IIB, and III that are useful as intermediates for the synthesis of other useful compounds. The invention provides for the use of compounds of Formulas I, II, IIB, and III for the manufacture of catalysts useful for cross-coupling reactions, such as carbon-oxygen bond-forming reactions. The invention provides for the use of compositions described herein for use in preparing reagents for cross-coupling reactions.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
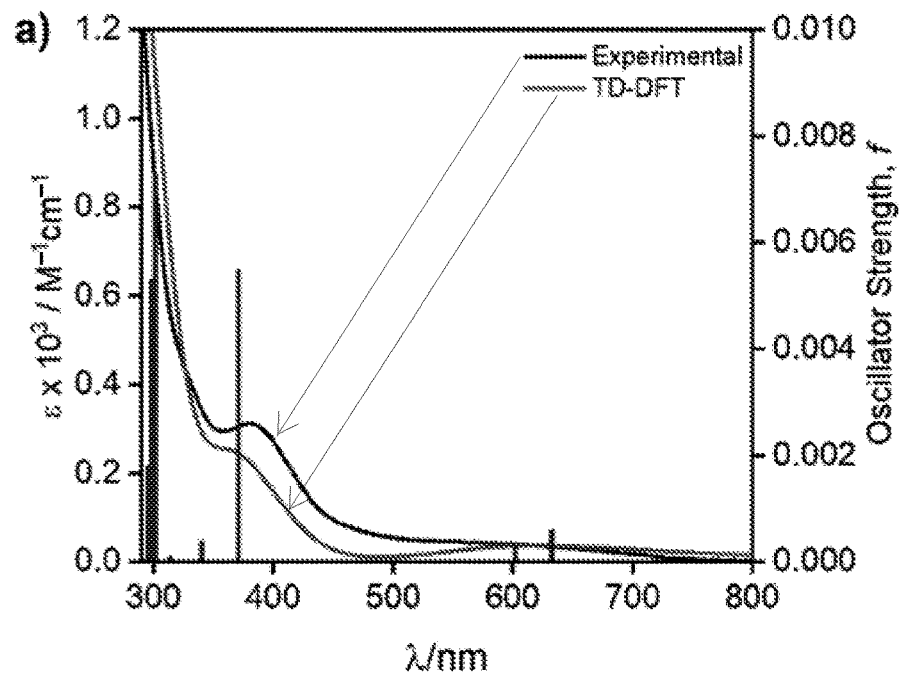
FIG. 1. (a) Experimental (top trace) and simulated (bottom trace) absorption spectrum of 1a with overlaid relevant oscillators (vertical bars) from TD-DFT calculations. (b) Natural transition orbitals (NTOs, 0.05 isocontour value) associated with the visible absorption bands 1a. (c) A simplified excited-state diagram for 1a, showing population of the lowest energy excited state, a $^3$MC d-d state.
Figure 1:
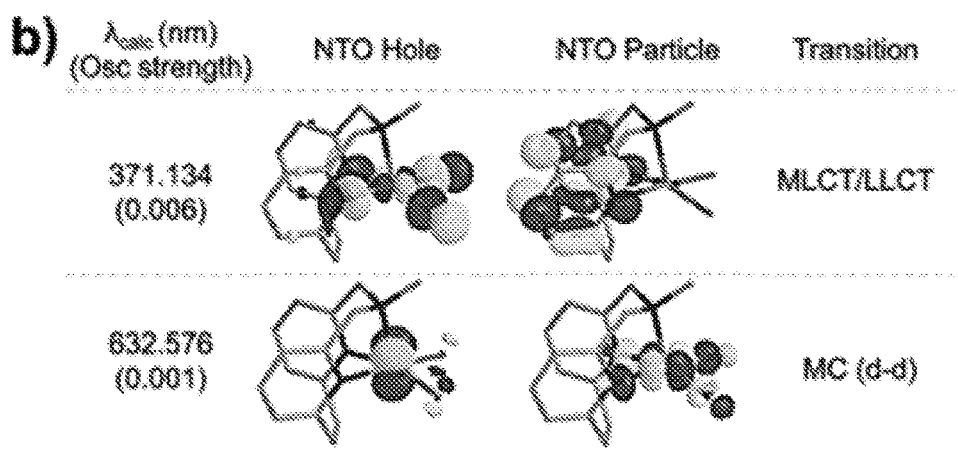
Figure 1:
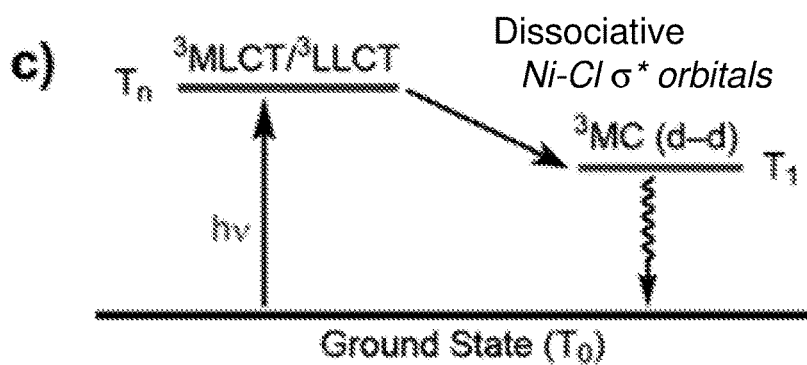

Photoredox catalysis has emerged as a powerful strategy for C—O cross-coupling reactions. Although the involvement of paramagnetic Ni(I) and Ni(III) species as active intermediates in the catalytic cycle has been proposed, a thorough spectroscopic investigation of these species is lacking. We herein report a new class of tridentate pyridinophane ligands $^R$N3 that allow for detailed mechanistic studies of the photocatalytic C—O coupling reaction. The derived ($^R$N3)Ni complexes are active C—O cross-coupling photocatalysts under mild conditions and without an additional photocatalyst. We also utilized the $^R$N3 ligands to study the essential but so far putative steps involving paramagnetic Ni species in the proposed catalytic cycle: the oxidative addition of an aryl bromide to a Ni(I) species, the ligand exchange at a Ni(III) center, and the C—O reductive elimination from a Ni(III) species. The present work also suggests these $^R$N3 ligands are a practical platform for mechanistic studies of related Ni-catalyzed reactions.

In addition to the Ni complexes, other transition metal complexes supported by the $^R$N3 ligands should also exhibit new reactivity. Based on the coordination flexibility of the $^R$N3 type ligand to accommodate metal ions having different sizes and oxidation states, we expect that a variety of other transition metal ions such as Cu, Co, Zn, Fe, Mn, Pd, Ru, Rh can also be readily supported. As such, the potentially rich chemistry of these complexes in many applications is expected, from small molecule activation (such as O$_2$, H$_2$, $CO_2$, and $H_2$), catalytic oxidation reactions, olefin polymerization catalysis, new compounds with desired photophysical properties.

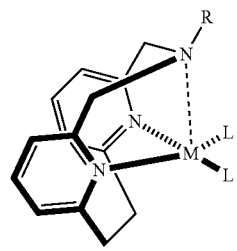

M = Ni, Cu, Co, Zn, Fe, Mn, Pd
L = F, Cl, Br, MeCN, OTf, Alkyl, Aryl ... etc

Additional information and data supporting the invention can be found in the following publication: *Nat. Commun.* 13, 1313 (2022) and its Supporting Information, which is incorporated herein by reference in its entirety.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, ... 9, 10. It also means 1.0, 1.1, 1.2. 1.3, ..., 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Ed., Cary and Sundberg (1983); for heterocyclic synthesis see Hermanson, Greg T., Bioconjugate Techniques, Third Ed., Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

An alkylene is an alkyl group having two free valences at a carbon atom or two different carbon atoms of a carbon chain. Similarly, alkenylene and alkynylene are respectively an alkene and an alkyne having two free valences at two different carbon atoms.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl group can be unsubstituted or substituted. The cycloalkyl group can be monovalent or divalent, and can be optionally substituted as described for alkyl groups. The cycloalkyl group can optionally include one or more cites of unsaturation, i.e., the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl and bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described below.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano.

Embodiments of the Technology

This disclosure provides an organometallic compound of Formula I:

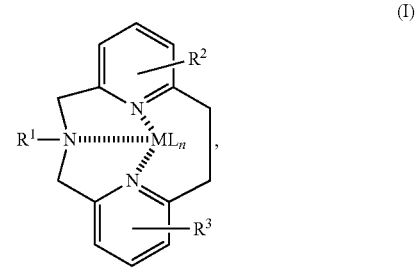

wherein
 M is a transition metal;
 L is a ligand and n is 1, 2, 3, 4, or 5;
 $R^1$ is —$(C_1\text{-}C_6)$alkyl, —$(C_3\text{-}C_6)$cycloalkyl, or —$(C_1\text{-}C_6)$alkyl$(C_3\text{-}C_6)$cycloalkyl; and
 $R^2$ and $R^3$ are each independently H, halo, —$(C_1\text{-}C_6)$alkyl, —$(C_3\text{-}C_6)$cycloalkyl, —O$(C_1\text{-}C_6)$alkyl, or —N[$(C_1\text{-}C_6)$alkyl]$_2$;
wherein each $(C_1\text{-}C_6)$alkyl moiety is independently unbranched or branched.

In various embodiments, M is Ni, Cu, Co, Zn, Fe, Mn, Pd, Ru or Rh. In other embodiments, M is Ni wherein Ni is Ni (II) or Ni (III). In various embodiments, L is halo, alkyl, aryl, nitrile, acetophenone or p-acetophenone, sulfonate, sulfonyl, toluenesulfonyl or p-toluenesulfonyl, or a combination thereof. In various embodiments, n is 2 or 3. In various embodiments, aryl is optionally substituted. In various embodiments, L, $R^1$, $R^2$ and $R^3$ are each independently methyl, ethyl, propyl, isopropyl, n-butyl, sec-butyl, or tert-butyl. In various embodiments, $R^2$ and $R^3$ are H.

In some embodiments, the compound is:

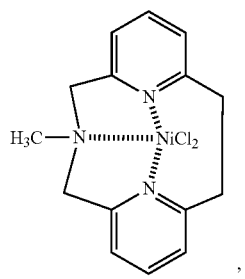

,

-continued

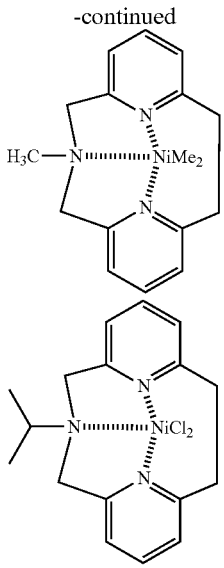

,

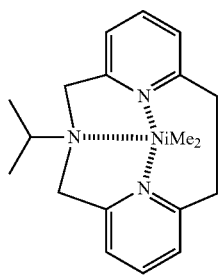

,

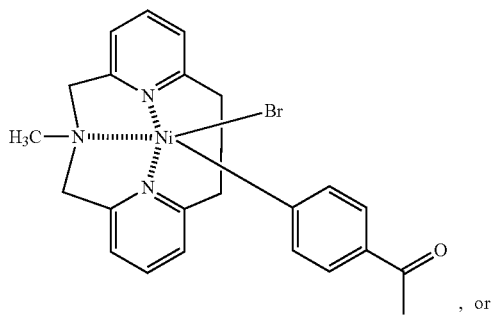

, or

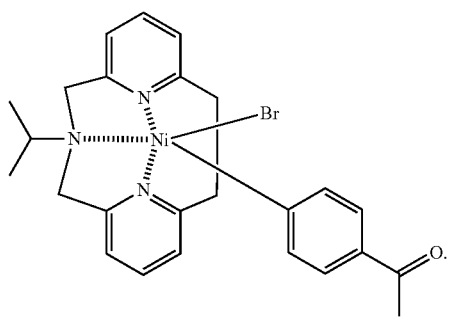

.

Also, this disclosure provides a macrocyclic compound of Formula II:

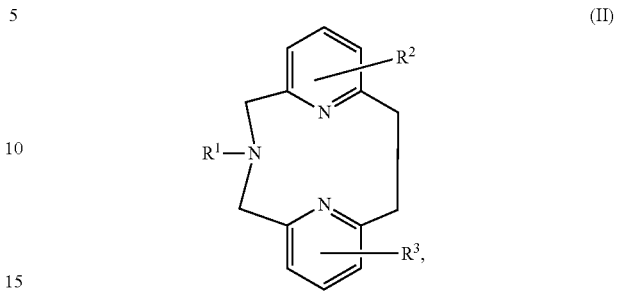

(II)

wherein: $R^1$ is —$(C_1$-$C_6)$alkyl, —$(C_3$-$C_6)$cycloalkyl, or sulfonyl; and $R^2$ and $R^3$ are each independently H, halo, —$(C_1$-$C_6)$alkyl, —$(C_3$-$C_6)$cycloalkyl, —$O(C_1$-$C_6)$alkyl, or —$N[(C_1$-$C_6)$alkyl]$_2$;

wherein each $(C_1$-$C_6)$alkyl moiety is independently unbranched or branched.

In various embodiments, $R^1$ is methyl, isopropyl, or arylsulfonyl. In various embodiments, $R^2$ and $R^3$ are H.

In some embodiments, the compound is:

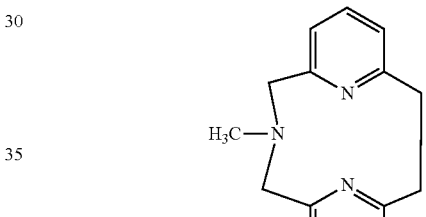

,

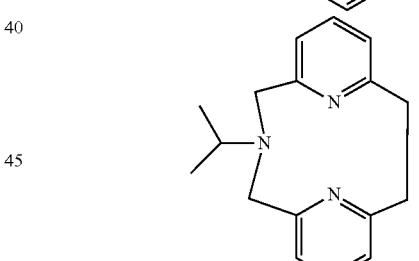

, or

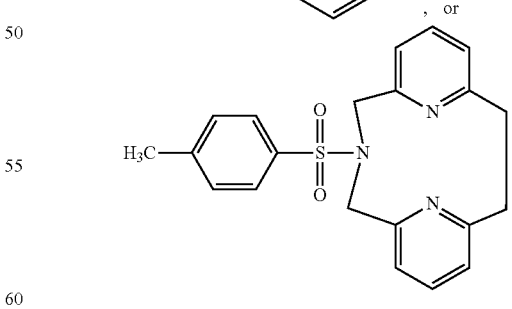

.

Additionally, this disclosure provides a composition comprising a compound disclosed herein and a suitable solvent. In various embodiments, the solvent may be polar, nonpolar, protic, aprotic, or a combination thereof. In various embodiments, the solvent is an ether, hydrocarbon, or a halogenated solvent. In some embodiments, the solvent is, for example, acetonitrile, tetrahydrofuran, dichloromethane, chloroform, pentane, hexane, toluene, ethanol, water, or a combination thereof when the combined solvents are miscible with each other.

In other embodiments, the compound is:

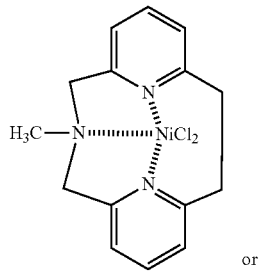

or

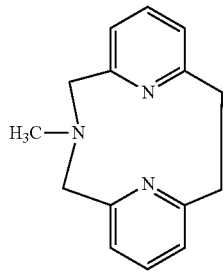

Furthermore, this disclosure provides a method for preparing a pyridinophane comprising:

a) contacting a compound of Formula III:

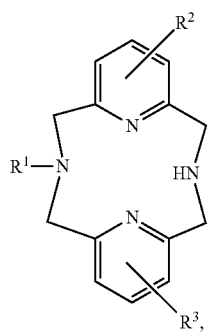

wherein: $R^1$ is a nitrogen protecting group; and
$R^2$ and $R^3$ are each independently H, halo, —$(C_1$-$C_6)$alkyl, —$(C_3$-$C_6)$cycloalkyl, —$O(C_1$-$C_6)$alkyl, or —$N[(C_1$-$C_6)$alkyl$]_2$; wherein each $(C_1$-$C_6)$alkyl moiety is independently unbranched or branched;
and nitrous acid (or a nitrite) to form a nitrosamine; and b) reducing the nitrosamine under suitable reaction conditions to form a pyridinophane of Formula IIB:

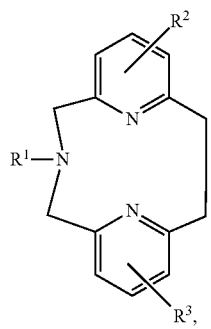

wherein $R^1$, $R^2$, and $R^3$ are as defined for Formula III.

In various embodiments, $R^1$ of the pyridinophane is para-toluenesulfonyl. In various embodiments, the protecting group is, for example, tosylate, acetate, 9-fluorenylmethyl carbamate, t-Butyl carbamate, or benzyl carbamate.

In some embodiments, the method further comprises:
c) removing the nitrogen protecting group from the pyridinophane of Formula IIB to form a secondary amine wherein $R^1$ is H;
d) alkylating the secondary amine to form a tertiary amine wherein $R^1$ is —$(C_1$-$C_6)$alkyl;
e) contacting the tertiary amine and a transition metal salt to form a transition metal complex of the pyridinophane having one or more ligands; and
f) optionally replacing ligands on the transition metal moiety of the complex with different ligands under suitable reaction conditions.

Additionally, this disclosure also provides a method for cross-coupling comprising:
a) contacting an alcohol, a halo or sulfonate or sulfonyl substituted aromatic compound, a catalytic amount of an organometallic compound disclosed herein, and a base to form a mixture; and
b) irradiating the mixture under suitable reaction conditions to cross-couple the alcohol and substituted aromatic to form a carbon-oxygen bond.

In some embodiments, the organometallic compound is:

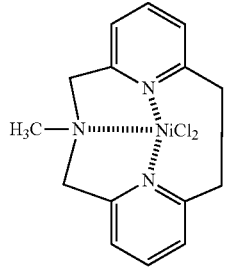

In various embodiments, the suitable reaction conditions comprise irradiating the mixture with light, a LED, or a purple light emitting diode (LED). In some embodiments, the LED emits light at a wavelength of about 390 nm.

Results and Discussion

Ligand Development. In 1958, Overberger et al. (*J. Am. Chem. Soc.* 1958, 80, 3009) reported the reduction of N-nitrosodibenzylamines by $Na_2S_2O_4$ to generate the hydrocarbon product with evolution of $N_2$. However, this reaction has received little attention since then, and only one report by Takemura et al. in 1988 exploited the N-nitroso reduction reaction to obtain [2.2]cyclophane derivatives (*Tet. Lett.* 1988, 29, 1031). We speculated that this N-extrusion reaction would provide an efficient synthetic pathway for tridentate pyridinophane ligands. Our synthesis starts with the unsymmetrical pryridinophane precursor N-tosyl-2,11-diaza [3.3](2,6)pyridionphane ($^{TsH}$N4, Scheme 2a) (*Org. Biomol. Chem.* 2017, 15, 9923). For the nitrosylation step, $^{TsH}$N4 was treated with HNO$_2$ to generate the N-nitroso intermediate $^{TsNO}$N4 85% yield. Subsequent reductive elimination of dinitrogen from the nitrosamine was performed with Na$_2$S$_2$O$_4$ under basic conditions, converting $^{TsNO}$N4 to $^{Ts}$N3 in 75% yield. Additional steps of detosylation and methylation or isopropylation afforded the alkylated ligand variants $^{Me}$N3 or $^{iPr}$N3 in ~45% overall yields, confirming that further functionalization can be easily achieved. The N-nitroso reduction conditions are mild, suggesting a broad functional group tolerance. Since all reaction steps do not require extensive purification and their yields are high, the development of this novel synthetic route provides an opportunity to access a variety of ligand structures by further functionalization or starting from different secondary amine precursors.

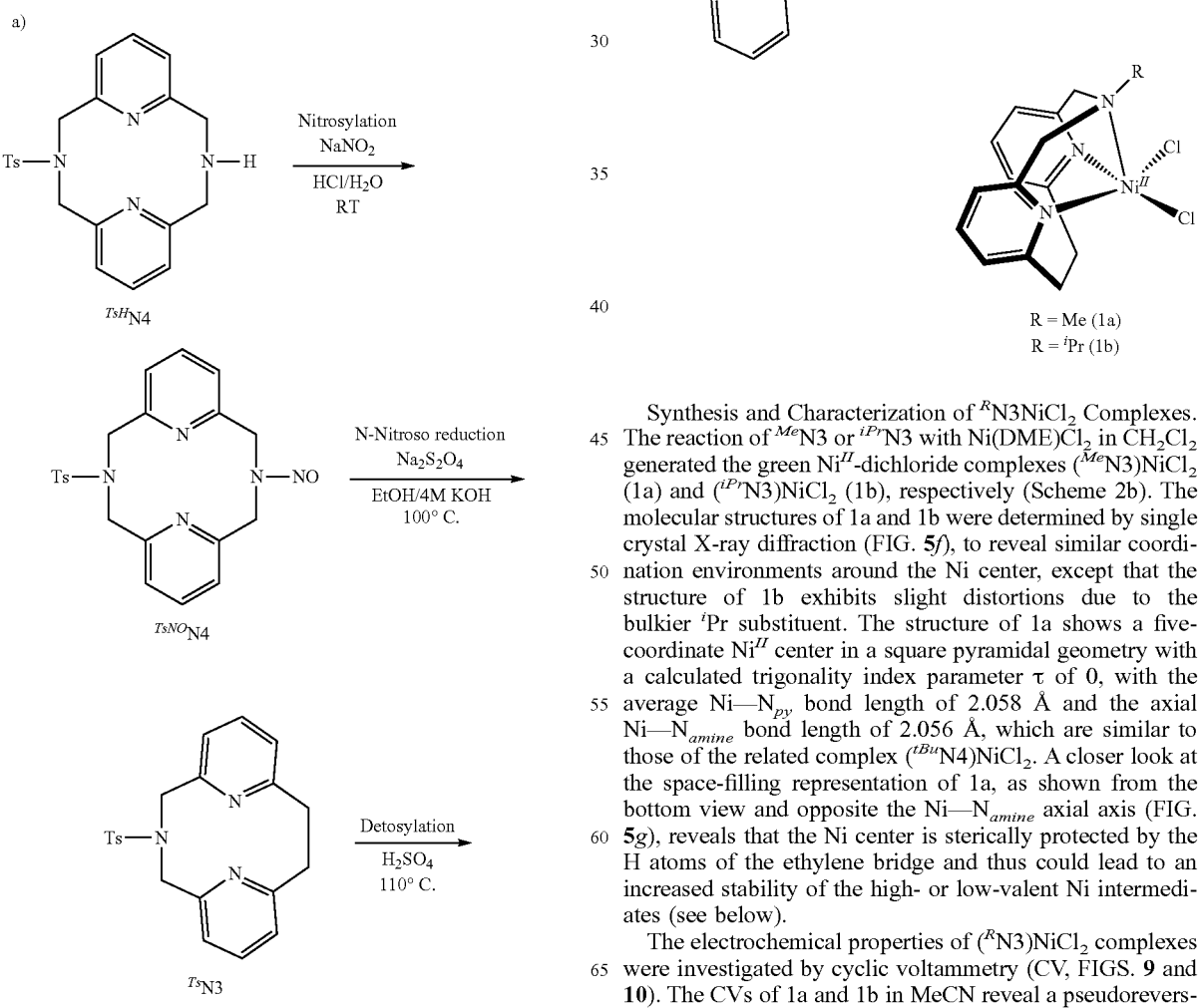

Scheme 2. (a) Synthesis of newly developed $^R$N3 type pyridinophane ligands. (b) Synthesis of ($^R$N3)NiCl$_2$ complexes (1a and 1b).

Figure 5:
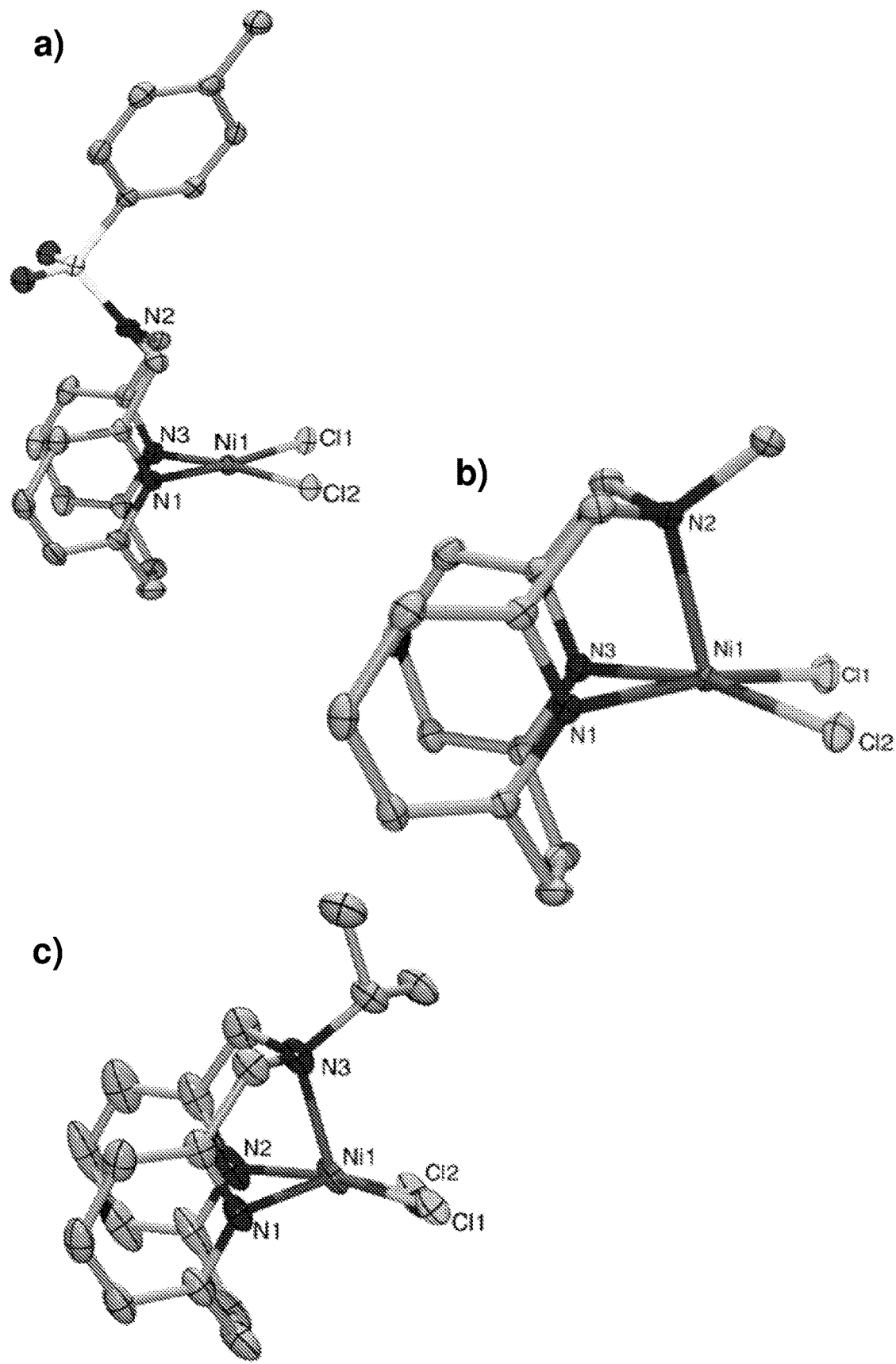
FIG. 5. (a) ORTEP representation of ($^{Ts}$N3)NiCl$_2$ with 50% probability thermal ellipsoids. (b) ORTEP representation of ($^{Me}$N3)NiCl$_2$ with 50% probability thermal ellipsoids. (c) ORTEP representation of ($^{iPr}$N3)NiCl$_2$ with 50% probability thermal ellipsoids. (d) ORTEP representation of ($^{Ts}$N3)NiMe$_2$ with 50% probability thermal ellipsoids. (e) ORTEP representation of ($^{Me}$N3)NiMe$_2$ with 50% probability thermal ellipsoids. (f) ORTEP representation of the 1a obtained by X-ray diffraction; (ellipsoid shown at 50% probability and hydrogen atoms omitted for clarity). Selected bond lengths (Å): Ni—N$_{py}$ 2.058, Ni—N$_{amine}$ 2.056, Ni—Cl 2.322. (g) Space-filling model of 1a highlighting the steric protection of the Ni metal center by the H atoms of the ethylene bridge.
Figure 5:
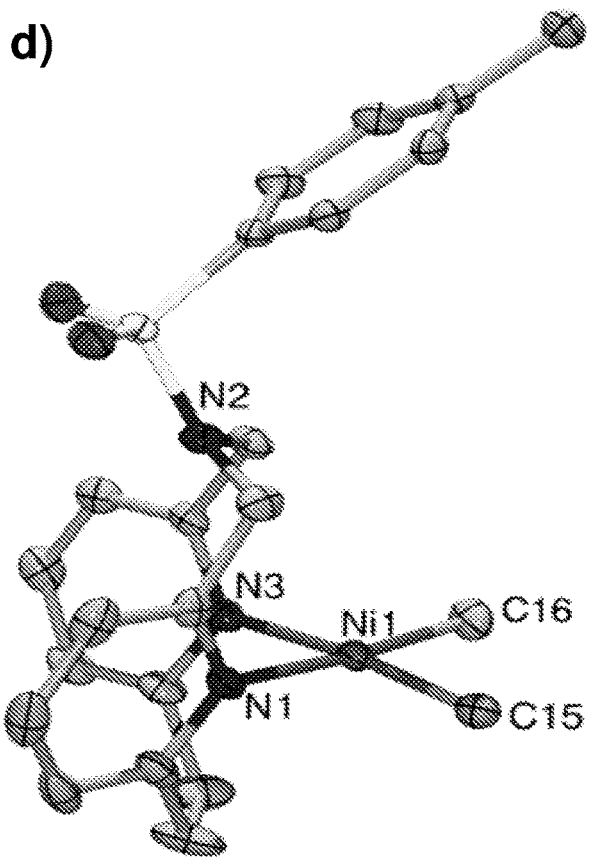
Figure 5:
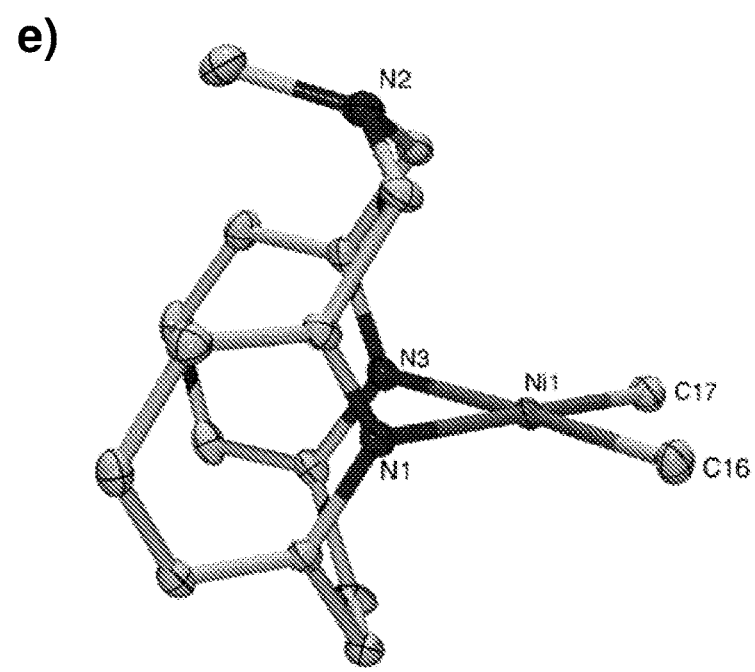
Figure 5:
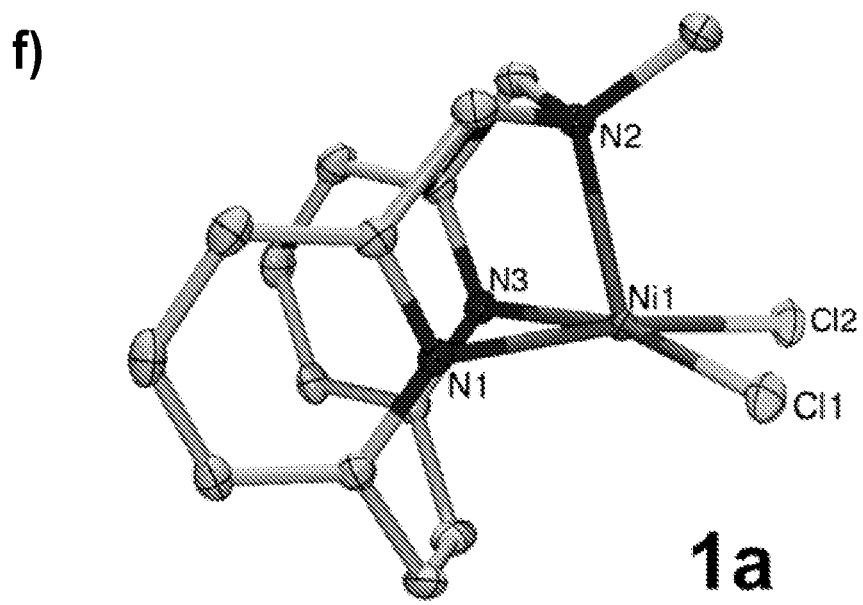
Figure 5:
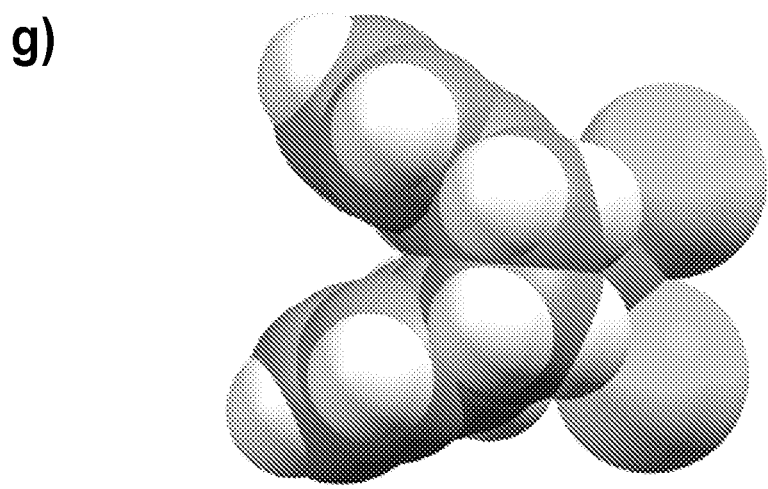
Figure 6:
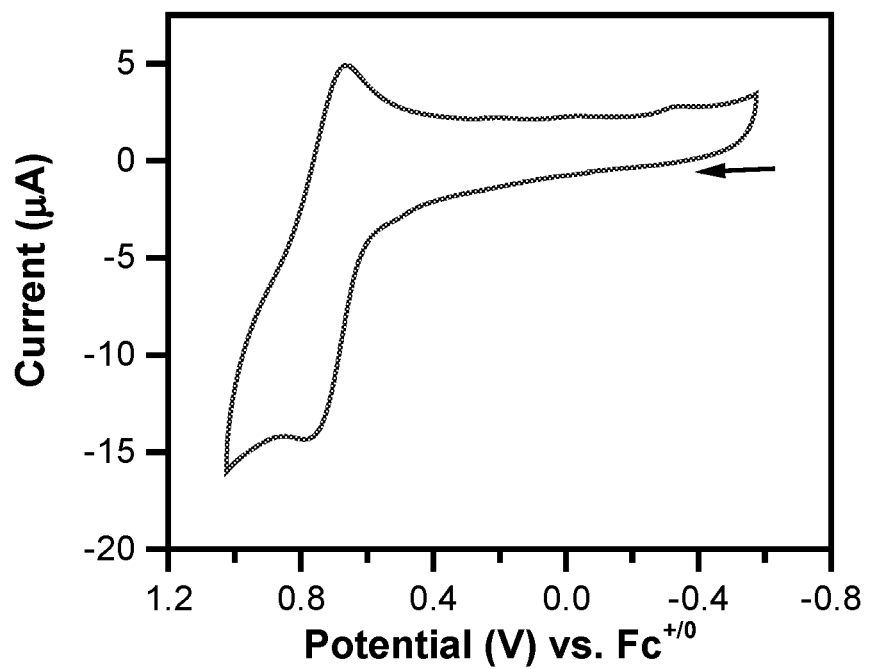
FIG. 6. Cyclic Voltammograms of ($^{Me}$N3)NiCl$_2$. Cyclic voltammetry experiments were performed in MeCN (0.1 M nBu$_4$NPF$_6$, scan rate: 100 mV/S), using a glassy carbon electrode as the working electrode, Pt wire as the auxiliary electrode, and the silver wire reference electrode.
Figure 6:
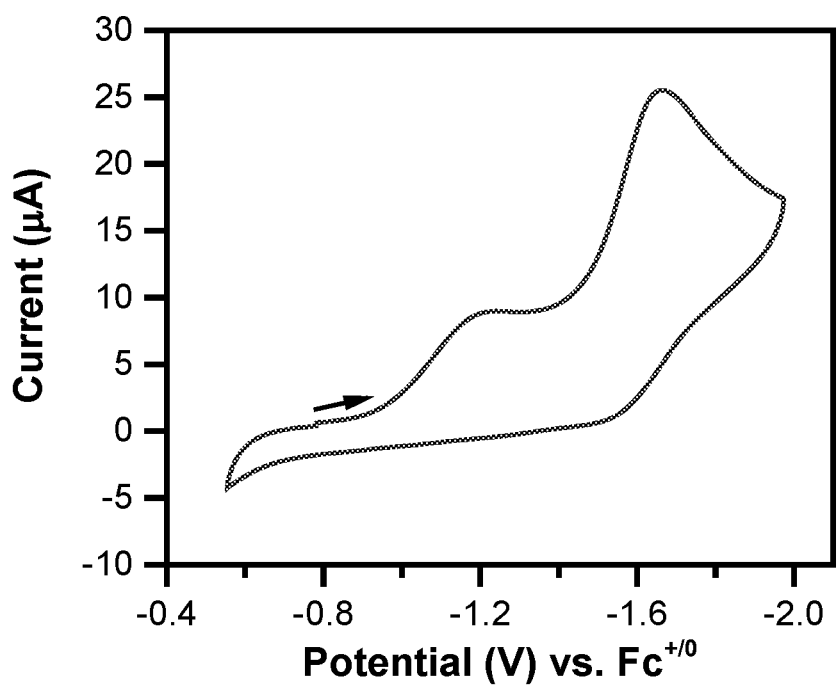
Figure 7:
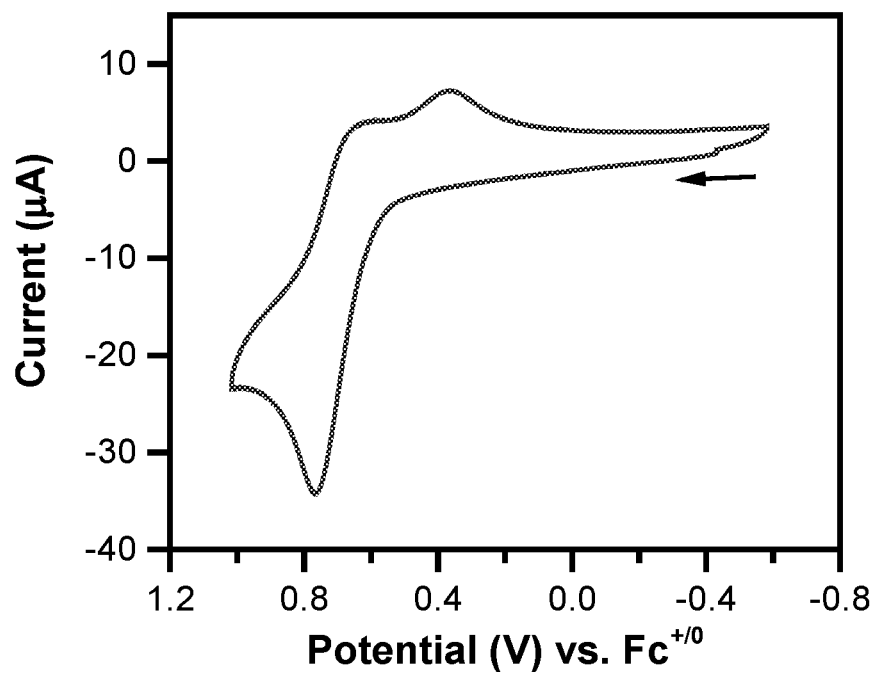
FIG. 7. Cyclic Voltammograms of ($^{iPr}$N3)NiCl$_2$. Cyclic voltammetry experiments were performed in MeCN (0.1 M nBu$_4$NPF$_6$, scan rate: 100 mV/S), using a glassy carbon electrode as the working electrode, Pt wire as the auxiliary electrode, and the silver wire reference electrode.
Figure 7:
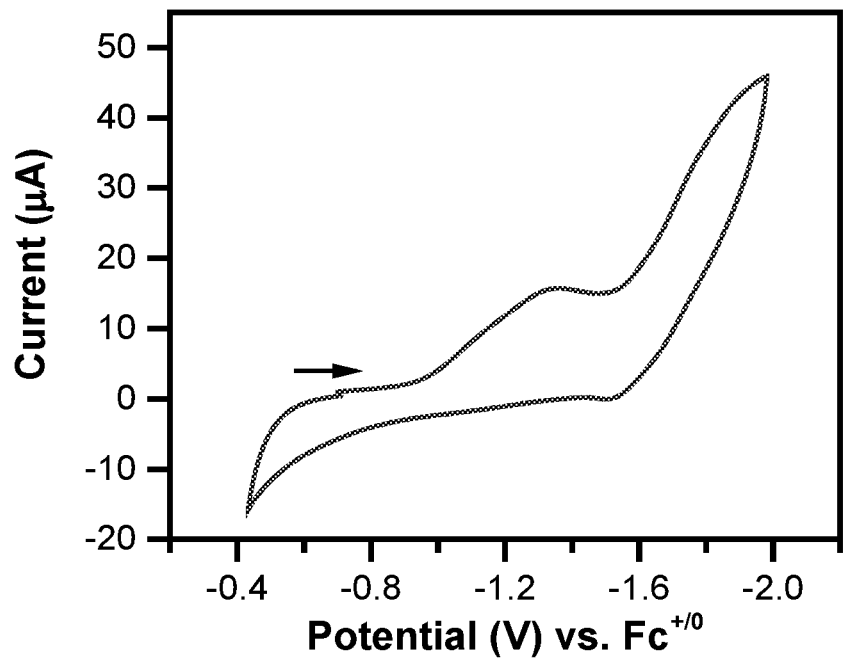

Synthesis and Characterization of $^R$N3NiCl$_2$ Complexes. The reaction of $^{Me}$N3 or $^{iPr}$N3 with Ni(DME)Cl$_2$ in CH$_2$Cl$_2$ generated the green Ni$^{II}$-dichloride complexes ($^{Me}$N3)NiCl$_2$ (1a) and ($^{iPr}$N3)NiCl$_2$ (1b), respectively (Scheme 2b). The molecular structures of 1a and 1b were determined by single crystal X-ray diffraction (FIG. 5*f*), to reveal similar coordination environments around the Ni center, except that the structure of 1b exhibits slight distortions due to the bulkier $^i$Pr substituent. The structure of 1a shows a five-coordinate Ni$^{II}$ center in a square pyramidal geometry with a calculated trigonality index parameter τ of 0, with the average Ni—N$_{py}$ bond length of 2.058 Å and the axial Ni—N$_{amine}$ bond length of 2.056 Å, which are similar to those of the related complex ($^{tBu}$N4)NiCl$_2$. A closer look at the space-filling representation of 1a, as shown from the bottom view and opposite the Ni—N$_{amine}$ axial axis (FIG. 5*g*), reveals that the Ni center is sterically protected by the H atoms of the ethylene bridge and thus could lead to an increased stability of the high- or low-valent Ni intermediates (see below).

Figure 8:
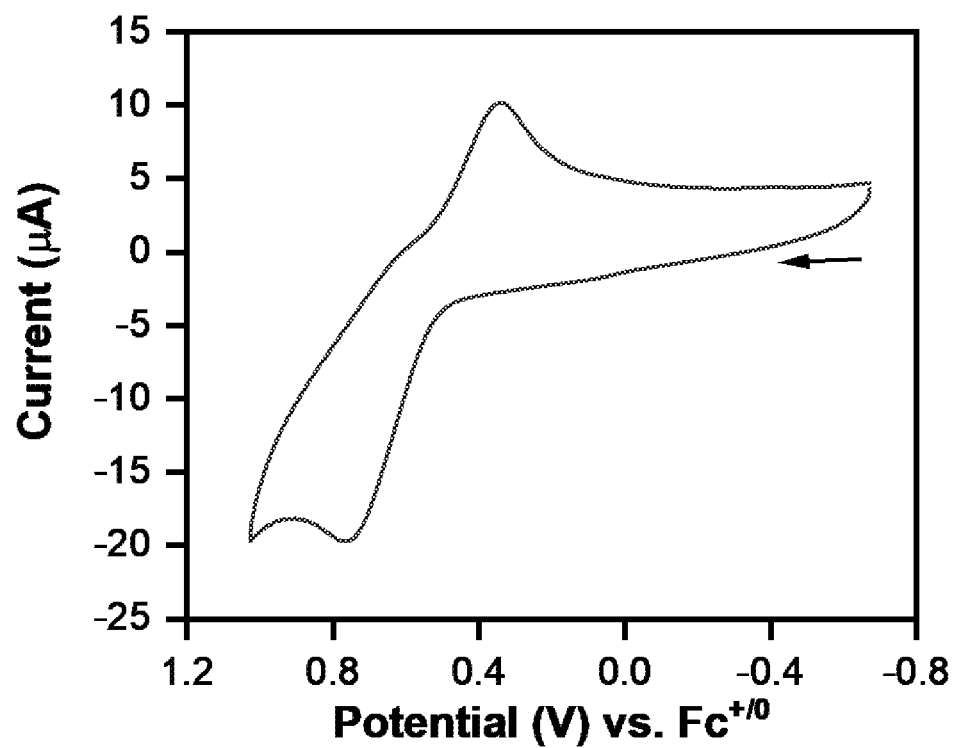
FIG. 8. Cyclic voltammograms of (dtbbpy)NiCl$_2$. Cyclic voltammetry experiments were performed in 0.1 M nBu$_4$NPF$_6$/MeCN (scan rate: 100 mV/s), using a glassy carbon electrode as the working electrode, Pt wire as the auxiliary electrode, and a silver wire reference electrode.
Figure 8:
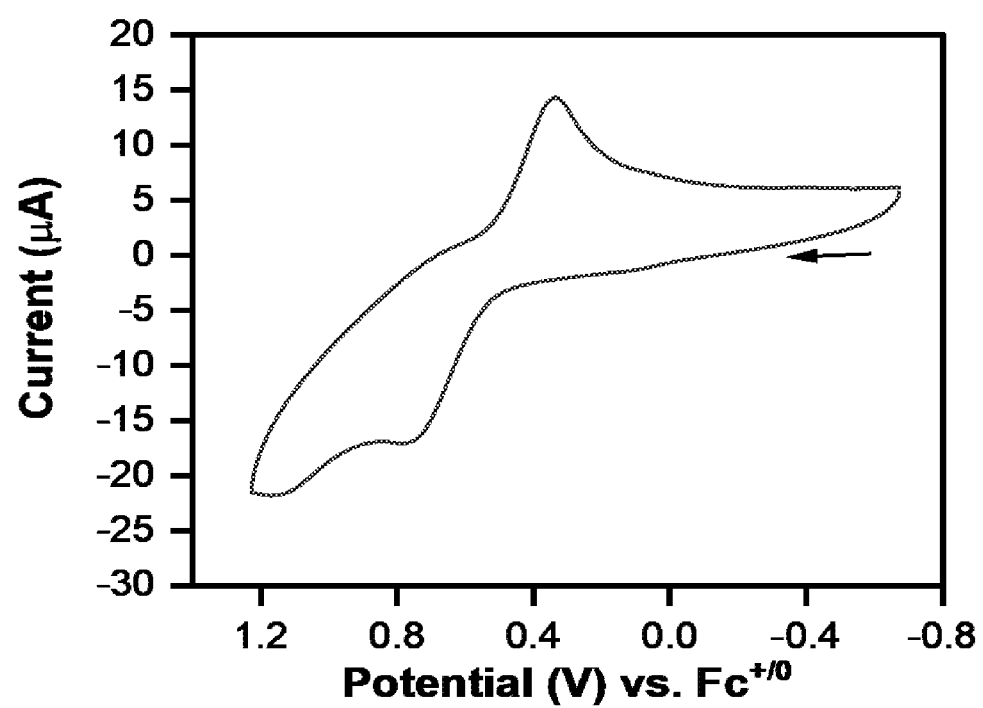
Figure 8:
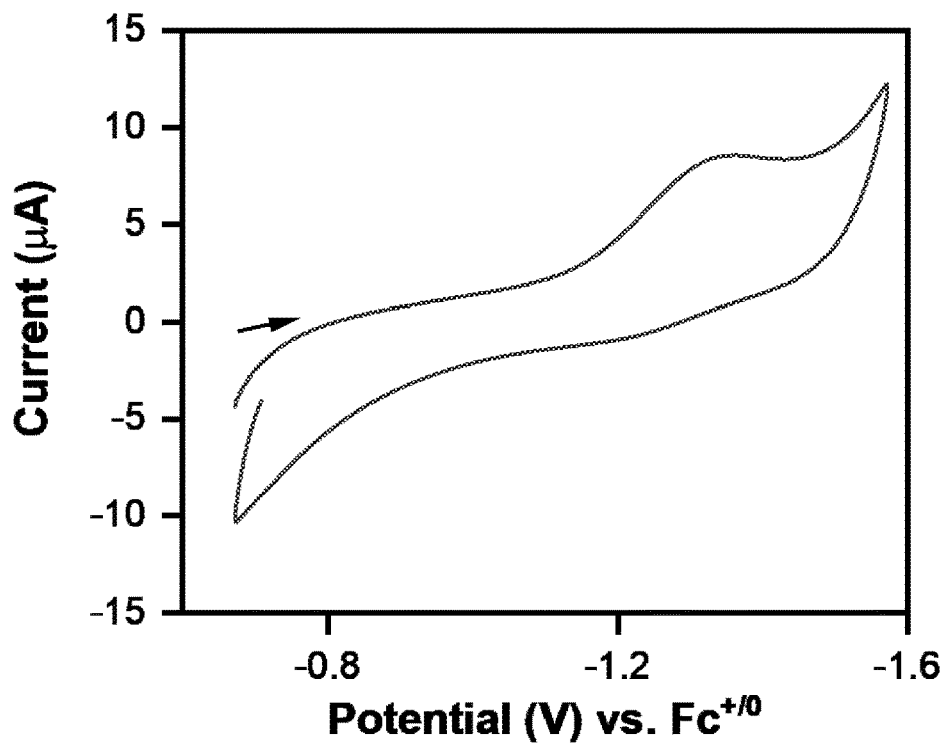
Figure 8:
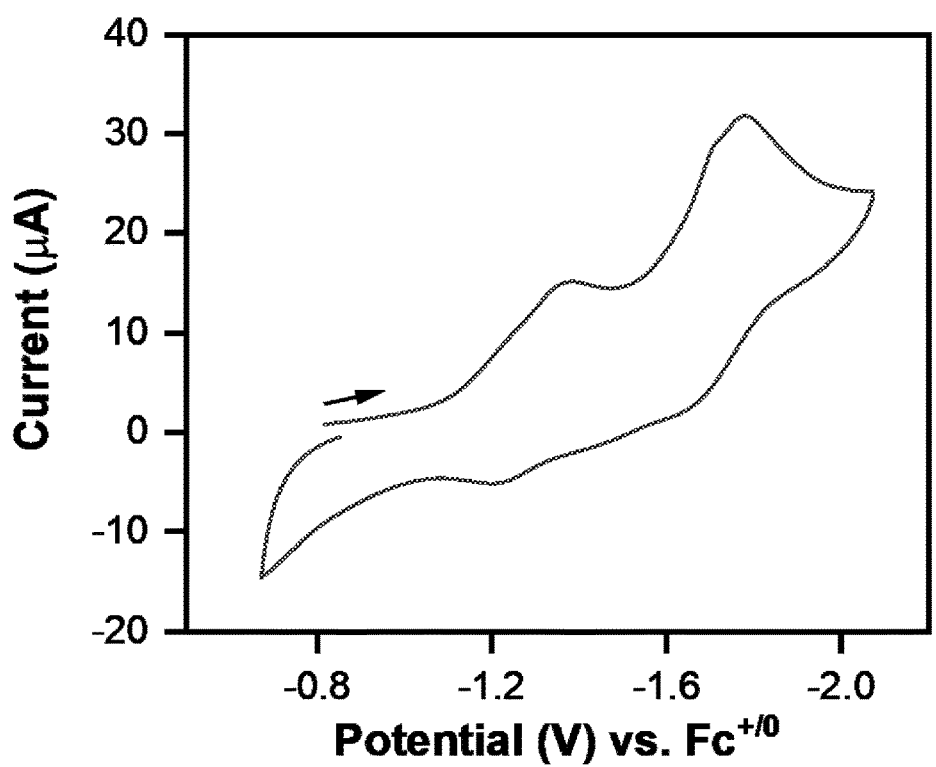
Figure 9:
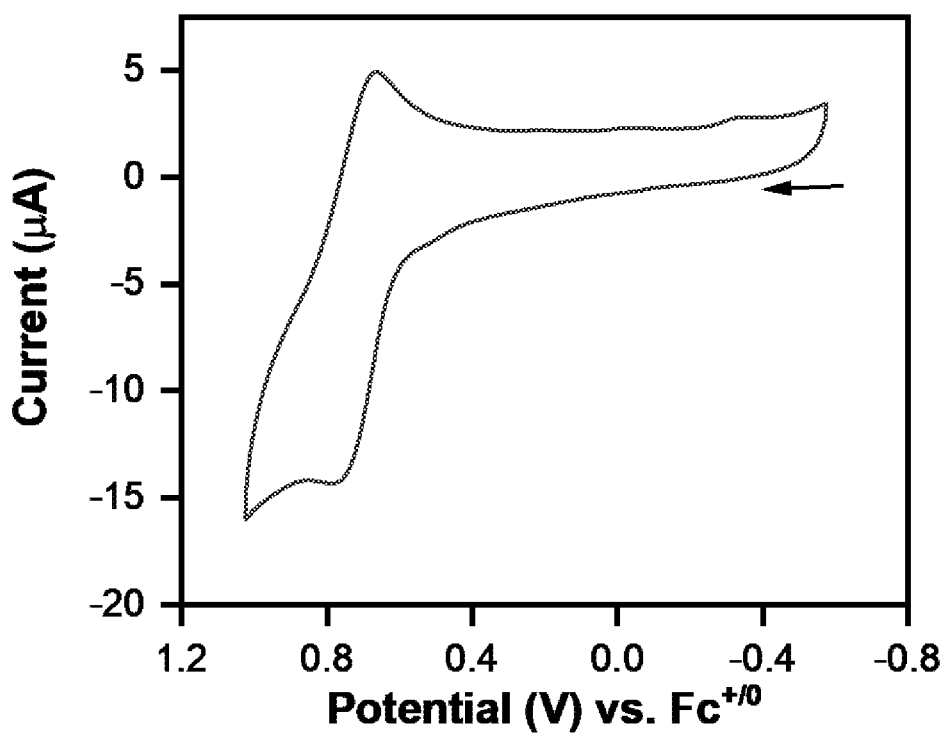
FIG. 9. Cyclic voltammograms of ($^{Me}$N3)NiCl$_2$ (1a), recorded at room temperature in 0.1 M nBu$_4$NPF$_6$/MeCN with a scan rate of 100 mV/s.
Figure 9:
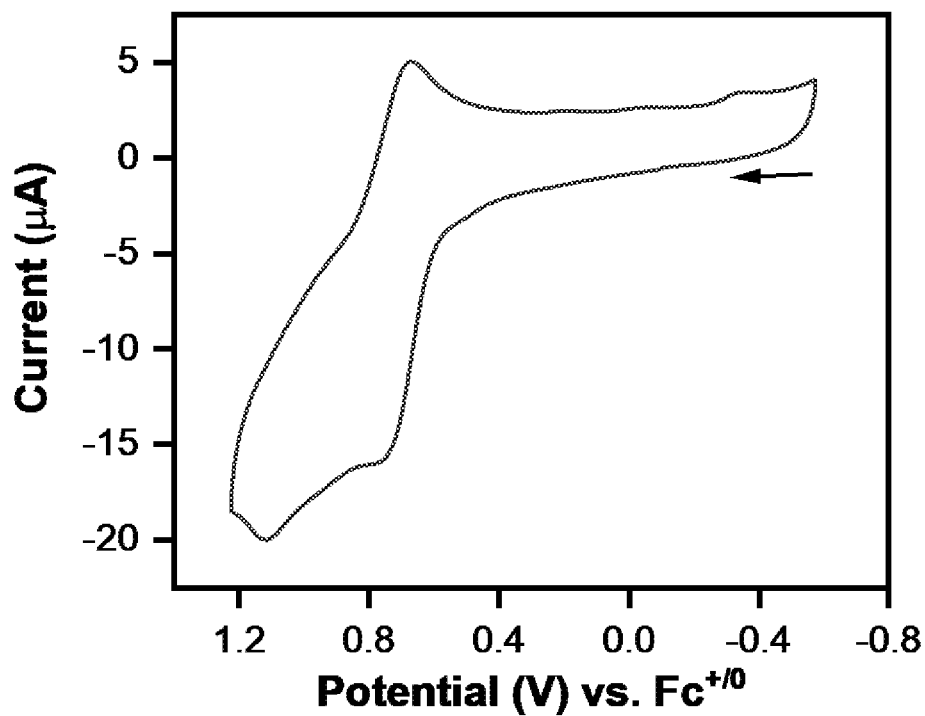
Figure 9:
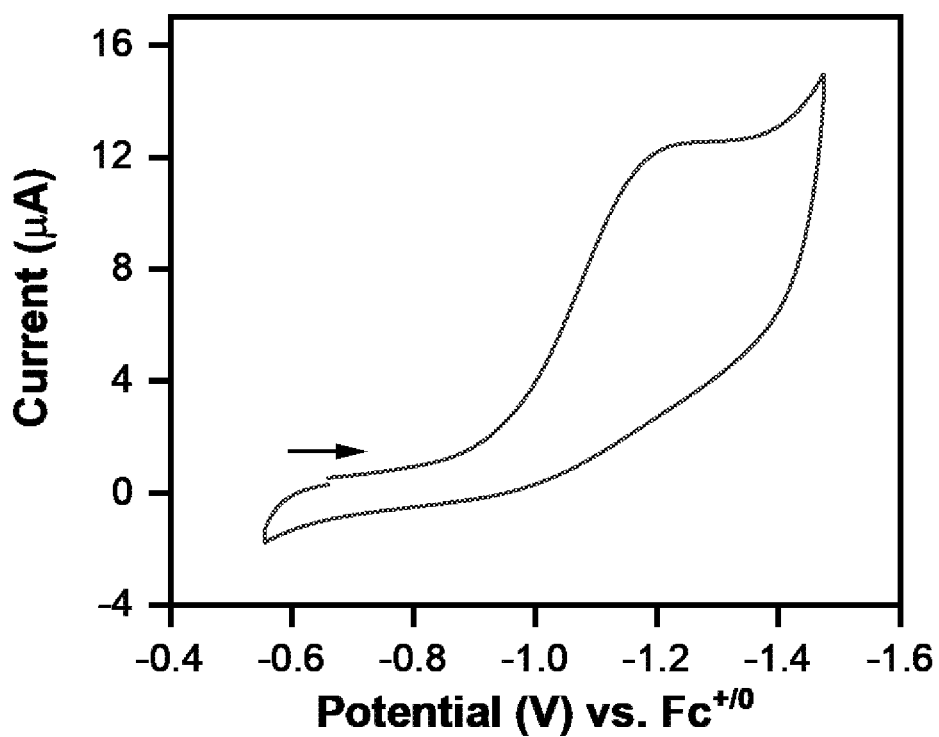
Figure 9:
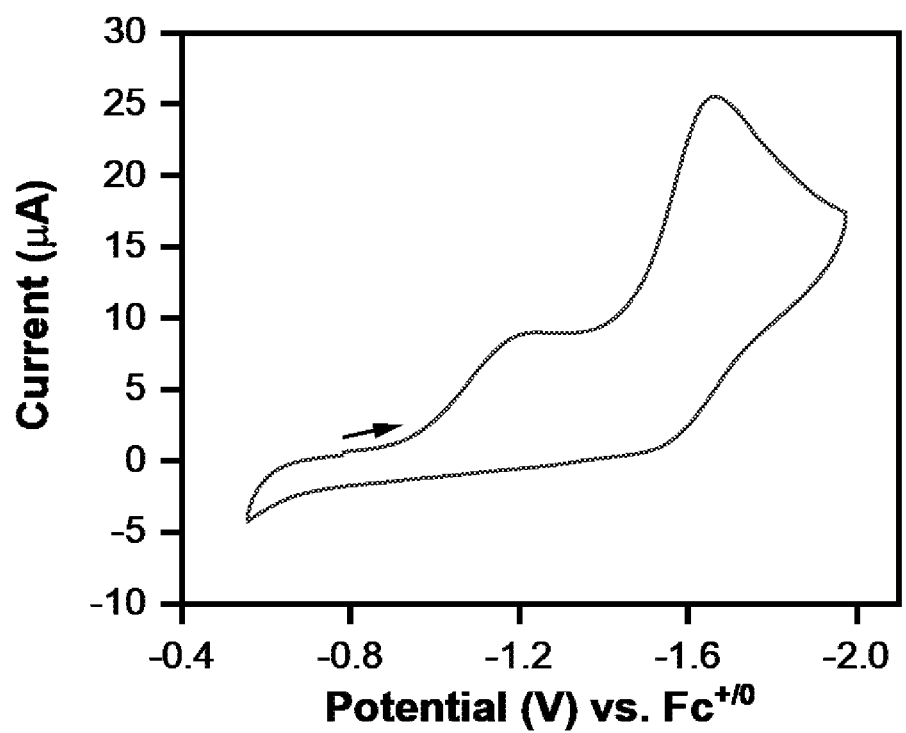
Figure 10:
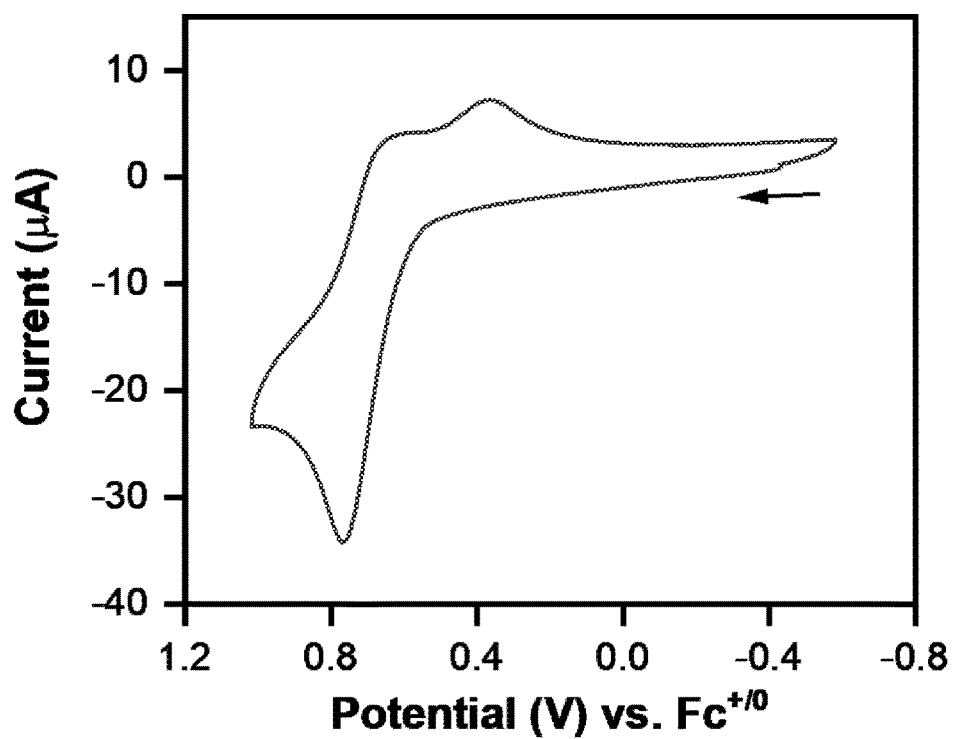
FIG. 10. Cyclic voltammograms of ($^{iPr}$N3)NiCl$_2$ (1b), recorded at room temperature in 0.1 M nBu$_4$NPF$_6$MeCN with a scan rate of 100 mV/s.
Figure 10:
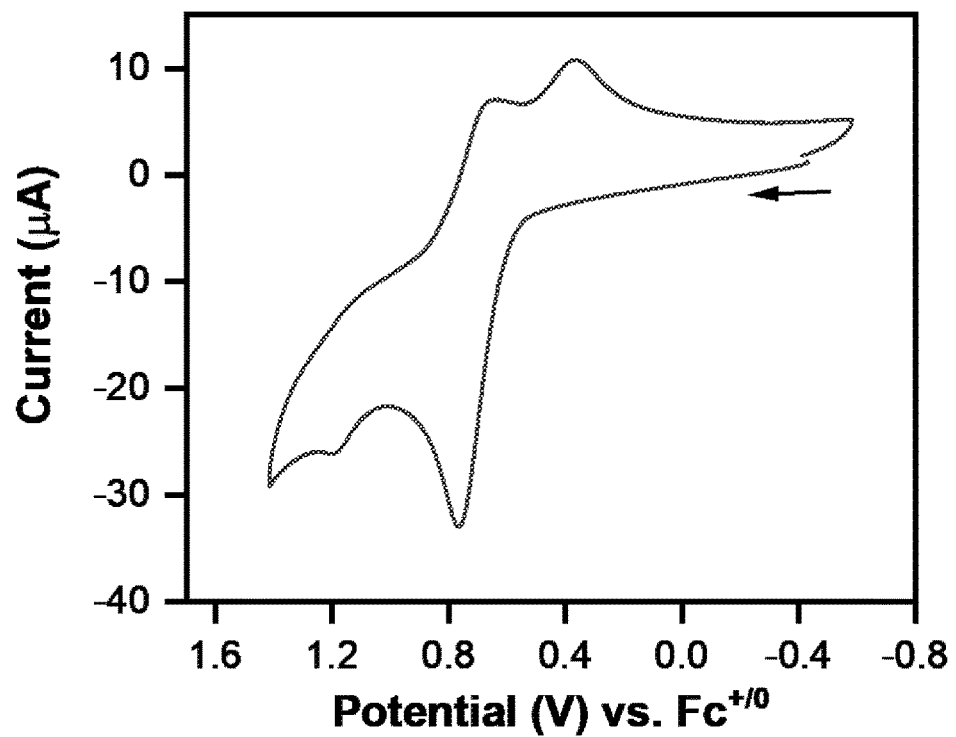
Figure 10:
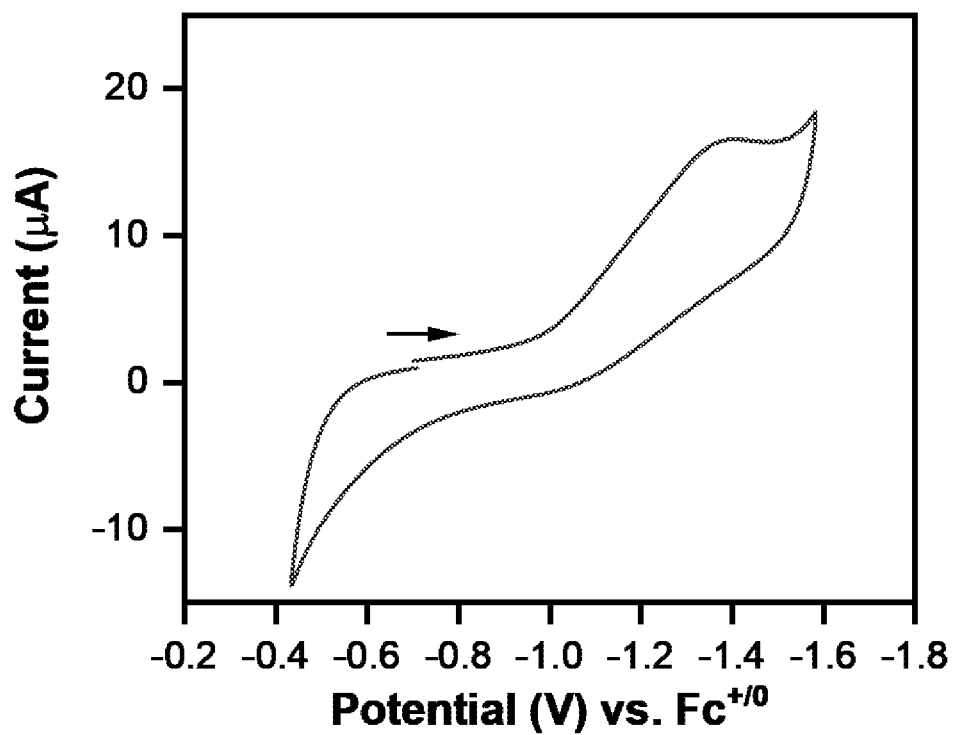
Figure 10:
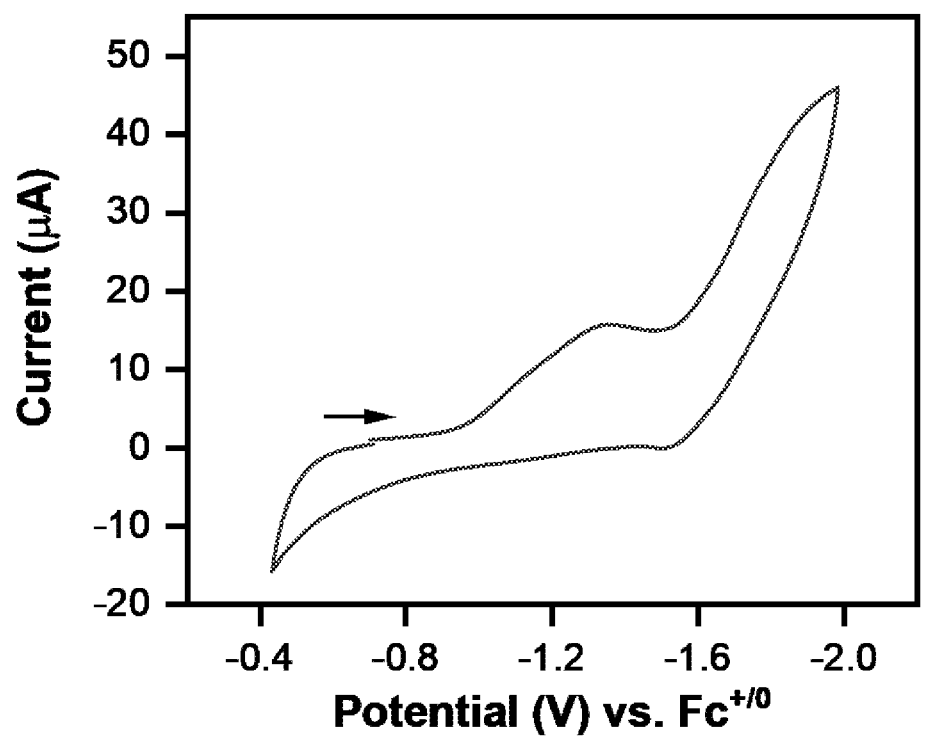

The electrochemical properties of ($^R$N3)NiCl$_2$ complexes were investigated by cyclic voltammetry (CV, FIGS. 9 and 10). The CVs of 1a and 1b in MeCN reveal a pseudoreversible oxidation wave at 0.71 V vs Fc$^{+/0}$, which is assigned to the $Ni^{III/II}$ couple, as well as an irreversible reduction wave at −1.20 V vs $Fc^{+/0}$ for 1a and −1.22 V for 1b, followed by a pseudoreversible reduction wave at −1.60 V vs $Fc^{+/0}$ for 1a and −1.72 V for 1b, respectively. It is important to note that the oxidation and reduction potentials for 1a and 1b are similar to those of (dtbbpy)NiCl$_2$, which exhibits an oxidation wave at 0.56 V vs $Fc^{+/0}$ and an irreversible reduction wave at −1.37 V vs $Fc^{+/0}$, followed by a pseudoreversible reduction wave at −1.74 V vs $Fc^{+/0}$ (FIG. 8). By comparison, while for $(^{tBu}N4)NiCl_2$ the $Ni^{III/II}$ oxidation event was observed at 0.52 V vs $Fc^{+/0}$, no reduction event was observed up to −2.00 V vs $Fc^{+/0}$, supporting our hypothesis that tetradentate ligands cannot stabilize $Ni^I$ species to a great extent.

The accessible reduction events observed for $(^RN3)NiCl_2$ indicates that for these complexes the $Ni^I$ oxidation state is accessible by one-electron reduction with a mild chemical reductant and can be exploited in reactivity and mechanistic studies. Overall, when compared to (dtbbpy)NiCl$_2$, the $(^RN3)NiCl_2$ complexes exhibit similar oxidation and reduction potentials, which is essential for photocatalysis, yet they possess a structural advantage by containing the flexible axial amine arm that is beneficial for detailed mechanistic studies.

The UV-visible absorption spectra of 1a and 1b were then obtained and analyzed computationally. The UV-vis absorption spectrum of 1a shows an intense band around 380 nm and a less intense band around 640 nm (FIG. 1). To probe the nature of the electronic transitions, time-dependent density functional theory (TD-DFT) calculations were performed. The higher energy absorption feature (380 nm) is attributed to a combination of a spin-allowed Cl→$^RN3$ ligand-to-ligand charge transfer ($^3$LLCT) and a Ni→$^RN3$ metal-to-ligand charge transfer ($^3$MLCT), while the lower energy absorption band (640 nm) is attributed to a metal-centered ($^3$MC) d-d electronic transition. The energy of the $^3$MC d-d transition (640 nm≈1.93 eV) is consistent with the electrochemical gap observed by CV (0.71 V−(−1.20 V)=1.91 eV), further supporting that the lowest excited state (T$_1$) has primarily MC d-d character.

Figure 12:
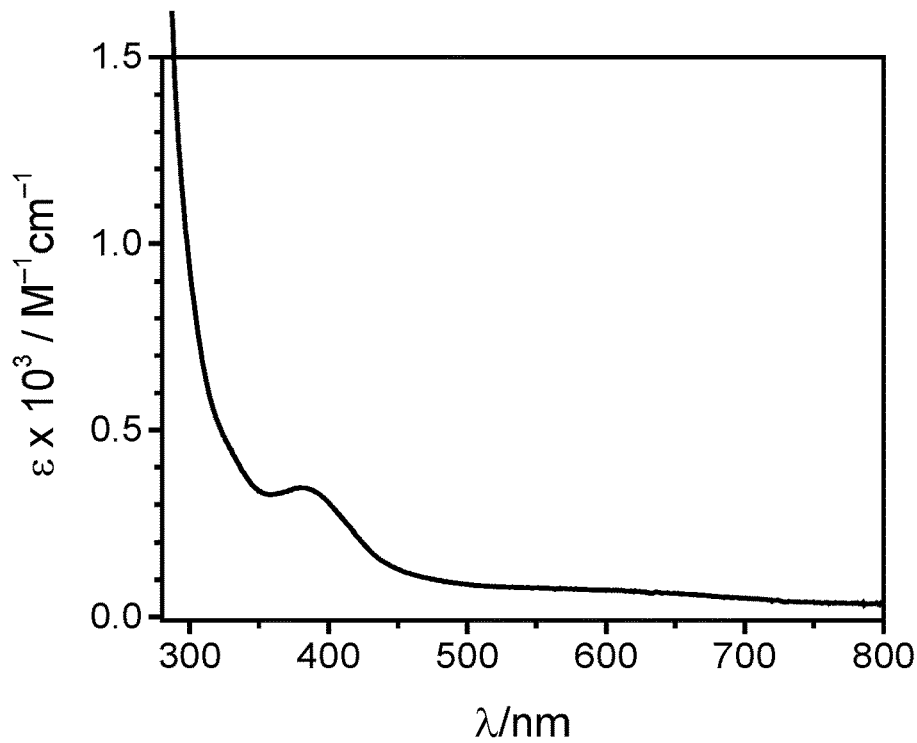
FIG. 12. UV-vis absorption spectra of ($^{Me}$N3)NiCl$_2$ in CH$_2$Cl$_2$.
Figure 13:
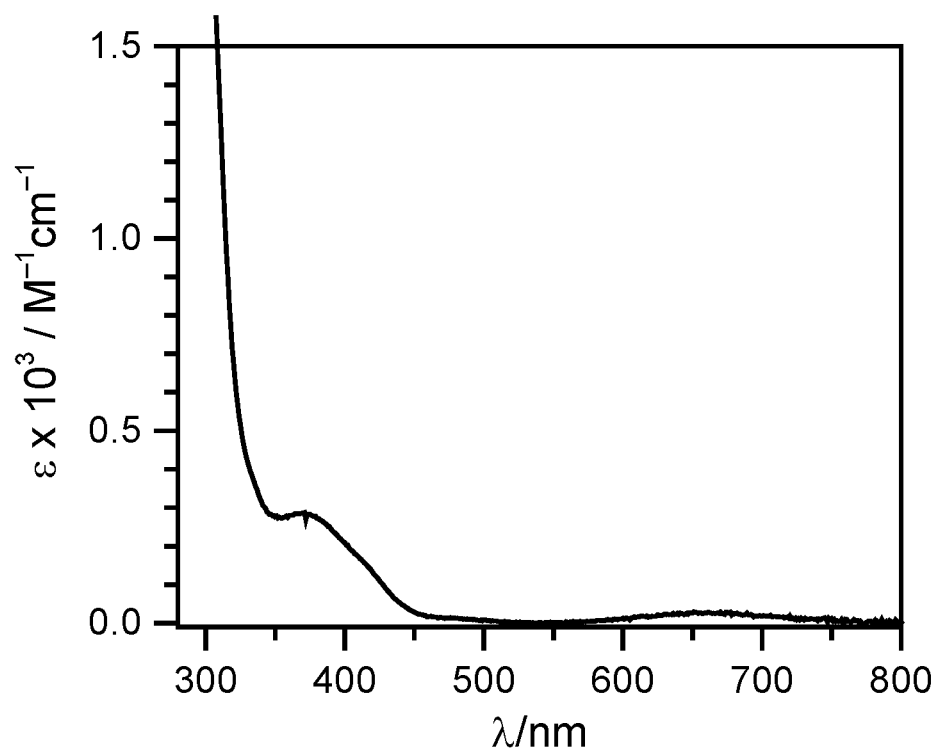
FIG. 13. UV-vis absorption spectra of ($^{iPr}$N3)NiCl$_2$ in CH$_2$Cl$_2$.

For a qualitative representation of the specified transitions between the ground and excited states, we performed natural transition orbital (NTO) analysis which provides a localized picture of the transition density matrix (FIG. 1b). NTO analysis supports that the 380 nm excitation the $T_n$ excited state with a mixed LLCT/MLCT character, while the 633 nm excitation involves electron transfer from the Ni atom to the Ni—Cl σ* orbitals, indicating a MC (d-d) transition. For general 3d-metal complexes, the MC (d-d) state is the lowest excited state owing to the intrinsically low ligand field strength, and the higher energy CT state and MC (d-d) state are close in energy, thus resulting in fast relaxation to the lowest-lying MC (d-d) state. Therefore, we propose that on initial population of the MLCT/LLCT state is followed by fast relaxation to the lower MC (d-d) state with an appreciable Ni—Cl σ* orbital population (FIG. 1c), which the promotes metal-ligand homolytic bond cleavage, as observed recently by Doyle for a similar Ni system (*J. Am. Chem. Soc.* 2020, 142, 5800). As 1a shows a prominent absorption band at 380 nm, a purple LED lamp (390 nm) was chosen as a light source for the direct light-promoted C—O coupling reaction (see below). Finally, the UV-vis absorption spectrum and TD-DFT calculation results for 1b are similar to those for 1a, indicating a minimal effect of the N-substituent on the electronic structure (FIGS. 12 and 13).

Photocatalytic C—O cross-coupling mediated by $(^RN3)$ NiCl$_2$ complexes. To probe the relevance of the $(^RN3)NiCl_2$ complexes in photocatalysis, we evaluated their light-promoted catalytic activity in C—O cross-coupling without any additional photocatalyst. Our initial efforts focused on optimizing the reaction conditions using methanol and 4-bromoacetophenone (Table 1 and Table 6-12). In the presence of 2 mol % $(^{Me}N3)NiCl_2$ (1a) and quinuclidine in THF, the desired C—O coupled product 4-methoxyacetophenone was obtained in 95% yield under purple LED irradiation (Table 1, entry 1). Control experiments revealed that the reaction did not proceed without Ni catalyst, light, or base (Table 1, entries 2-4). The desired product was not observed when the reaction was irradiated with blue LED, suggesting the crucial role of the excitation energy (Table 1, entry 5). While inorganic bases such as $K_2CO_3$ were not effective, possibly due to the slow proton-transfer kinetics or the precipitation of halides required to stabilize the $Ni^I$ intermediate, DABCO was effective but proceeded at a slightly slower rate and thus requiring a longer reaction times (Table 1, entries 6-8). Switching from 1a to 1b or $(^{Me}N3)NiBr_2$, lowering of catalyst loading to 0.2 mol %, or the addition of $^{Me}N3$ and Ni(DME)Cl$_2$ separately instead of 1a gave comparable yields (Table 1, entries 9-12). Notably, a 0.2 mol % catalyst loading is significantly less (~25-50 fold decrease) than the loadings used in other Ni-photocatalyzed C—O cross-couplings. Moreover, other alcohols such as 1-hexanol and benzyl alcohol could also be employed (Table 11, 86-90% product yield). However, the combination of 1a and heterogenous Zn$^0$ or Mn$^0$ without light was ineffective in our conditions, likely due to the slow electron transfer kinetics or insufficient generation of the active species during catalysis.

TABLE 1

Light-promoted Ni catalysis Reaction Development and Optimization.$^a$

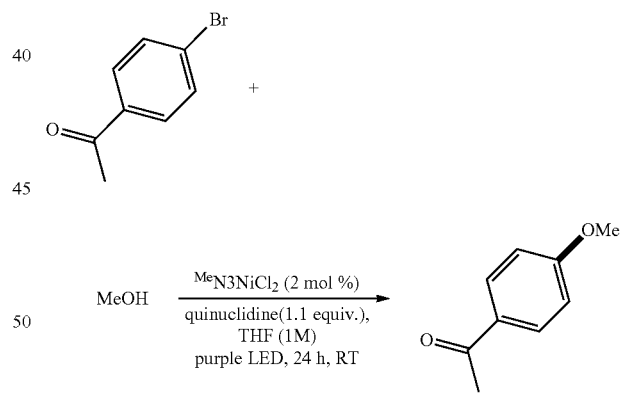

| Entry | Variation from the standard conditions | Yield (%) |
|---|---|---|
| 1 | none | 95 |
| 2 | no light (dark) | 0 |
| 3 | no $^{Me}N3NiCl_2$ | 0 |
| 4 | no base | 0 |
| 5 | Blue LED instead of purple LED | 0 |
| 6 | DABCO instead of quinuclidine, 24 h | 77 |
| 7 | DABCO instead of quinuclidine, 36 h | 96 |
| 8 | $K_2CO_3$ instead of quinuclidine | 0 |
| 9 | $^{Me}N3NiCl_2$ 0.2 mol % instead of 2 mol % | 90 |
| 10 | $^{Me}N3NiBr_2$ instead of $^{Me}N3NiCl_2$ | 90 |

TABLE 1-continued

| 11 | $^{iPr}$N3NiCl$_2$ instead of $^{Me}$N3NiCl$_2$ | 82 |
|----|---|----|
| 12 | $^{Me}$N3 (2 mol %) + Ni(DME)Cl$_2$ (2 mol %) instead of $^{Me}$N3NiCl$_2$ | 77 |
| 13 | ($^{Me}$N$_4$)NiCl$_2$ instead of ($^{Me}$N$_3$)NiCl$_2$ | 2 |

[a]Reaction conditions: In a N$_2$-filled glovebox, 4-bromoacetophenone (0.4 mmol, 1.0 equiv), quinuclidine (0.44 mmol, 1.1 equiv), MeOH (1.6 mmol, 4 equiv), ($^{Me}$N3Ni)Cl$_2$ (2 mol %) and a magnetic stir bar were added into 0.4 mL THF in a vial. The vial was irradiated with one purple LED lamp (52 W, 390 nm) under fan cooling. After 24 h, 1,3-benzodioxole (0.4 mmol) was added to the reaction mixture as a standard and the residue was analyzed by $^1$H NMR and GC-FID to determine the yield of C—O coupled product.

The use of a Ni complex supported by another tridentate N-donor ligand 1,4,7-triosopropyl-1,4,7-triazacyclononane, (iPr$_3$TACN)Ni$^{II}$Cl$_2$, generated the desired product only in a moderate yield (51%, see Ni catalyst Table 4), while the ($^R$N4)Ni$^{II}$Cl2 complex supported by the tetradentate ligand MeN4 yielded a negligible amount of product, validating our ligand design principle (Table 1, entry 13).

The same C—O coupling reaction was also probed under common dual Ni/photoredox catalytic conditions using various Ir or Ru photocatalysts and blue LED light ($\lambda_{max}$=456 nm) (Table 2). The photocatalyst screening experiments revealed that the Ir photocatalysts tested here gave the desired C—O coupled product in 80-98% yield, while the Ru catalysts showed no reactivity.

TABLE 2

Photoredox/Ni dual catalysis Reaction Optimization.[a]

MeOH + 4-bromoacetophenone → 4′-methoxyacetophenone $^{Me}$N3NiCl$_2$ (2 mol %)
Photocatalyst (0.5 mol %)
quinuclidine (1.1 equiv.),
THF (1M)
blue LED, 24 h, RT

| Entry | Photocatalyst | Yield (%) |
|---|---|---|
| 1 | no photocatalyst | 0 |
| 2 | [Ir(dF(CF$_3$)$_2$ppy)(dtbbpy)]PF$_6$ | 86 |
| 3 | Ir(ppy)$_3$ | 90 |
| 4 | [Ir(ppy)$_2$(dtbbpy)]PF$_6$ | 98 |
| 5 | [Ru(phen)$_3$]Cl$_2$ | ~1% |
| 6 | [Ru(bpz)$_3$](PF$_6$)$_2$ | 0 |

[a]Reaction conditions: In a N$_2$-filled glovebox, 4-bromoacetophenone (0.4 mmol, 1.0 equiv), quinuclidine (0.44 mmol, 1.1 equiv), MeOH (1.6 mmol, 4 equiv), ($^{Me}$N3)NiCl$_2$ (2 mol %), photocatalyst (0.5 mol %) and a magnetic stir bar were added into 0.4 mL THF in a vial. The vial was irradiated with one blue LED lamp (50 W, 456 nm) under fan cooling. After 24 h, 1,3-benzodioxole (0.4 mmol) was added to the reaction mixture as a standard and the residue was analyzed by $^1$H NMR and GC-FID to determine the yield of C—O coupled product.

Figure 11:
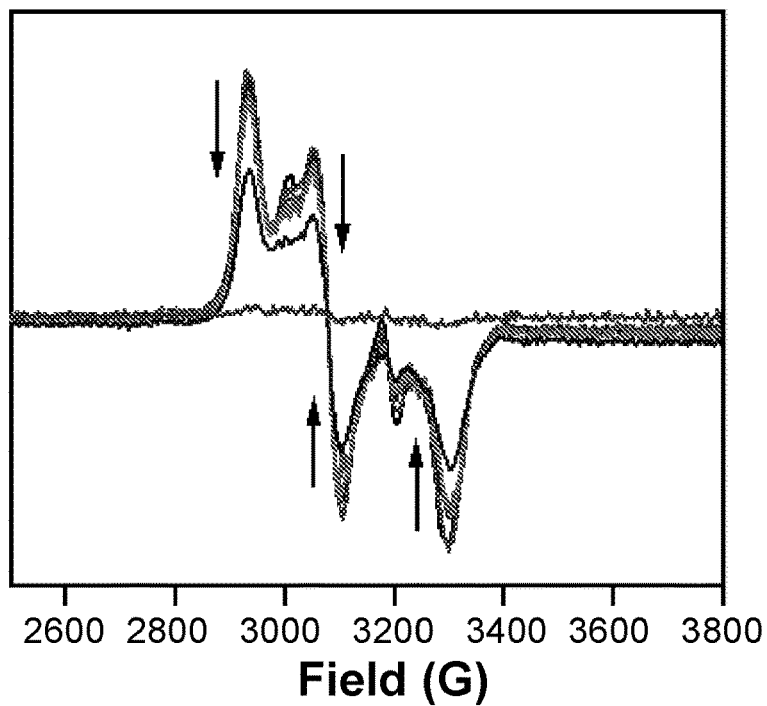
FIG. 11. EPR signal decays of 1b+CoCp*$_2$+20 equiv 4-bromoacetophenone over time. Each spectrum was recorded in MeOH/PrCN at 77 K, after quick thawing to −95° C. and subsequent refreezing.

EPR and reactivity studies. Recent reports have proposed the oxidative addition to Ni$^I$ to generate Ni$^{III}$ species is a key step in the C—O cross-coupling catalytic cycle, yet minimal evidence was provided and such a step has been underexplored experimentally. Our Ni catalysts have accessible Ni$^{II/I}$ redox potentials, thus we aimed to probe both the reduction of Ni$^{II}$ to a Ni$^I$ species and the subsequent oxidative addition of Ar—Br to generate a Ni$^{III}$ intermediate by using X-band electron paramagnetic resonance (EPR) spectroscopy. For the EPR studies, 1b was used due to its better solubility vs 1a. Upon the reduction of 1b by 1 equivalent decamethylcobaltocene (CoCp*$_2$) at −95° C. (FIG. 2a), a Ni$^I$ species 2 was formed that exhibits a rhombic EPR spectrum with g$_x$=2.241, g$_y$=2.113, and g$_z$=2.049 (FIG. 2d), indicating the presence of a metal-based radical. When 20 equiv 4-bromoacetophenone were added to a thawing solution of 2 (FIG. 2b), signals originating from two different species, tentatively assigned to the initial Ni$^I$ and a new Ni$^{III}$ species (in a 0.6:1 Ni$^I$:Ni$^{III}$ ratio) appeared in the EPR spectrum (FIG. 2e and FIG. 11).

The Ni$^{III}$ species is believed to be a transient 6-coordinate ($^{iPr}$N3)Ni$^{III}$(PhAc)BrCl (3) complex generated through the oxidative addition of 4-bromoacetophenone to 2. Moreover, when 40 equiv 4-bromoacetophenone were added to 2 (FIG. 2c), only a rhombic EPR signal with g$_x$=2.298, g$_y$=2.197, and g$_z$=2.037 formed (FIG. 2f), which was assigned to 3 and thus strongly supports a direct conversion from Ni$^I$ (2) to Ni$^{III}$ (3) that is promoted by the excess aryl halide. The observed EPR signals decay quickly upon warming up the solution for seconds at −80° C. (FIG. 11), supporting their increased reactivity and proposed involvement in catalysis. Finally, it is important to note that to the best of our knowledge the direction observation of the oxidation addition of an aryl halide to a Ni$^I$ species to generate a Ni$^{III}$ species has not been reported to date.

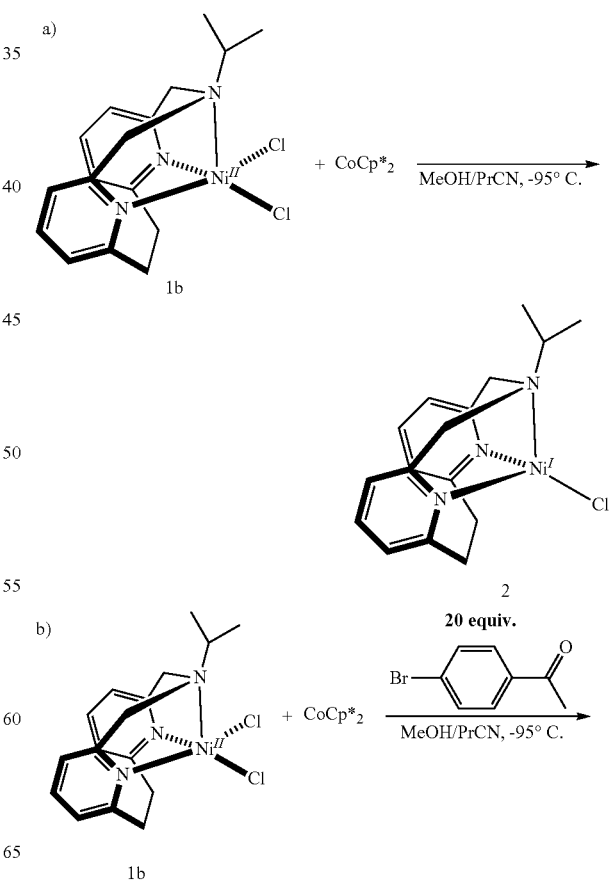

Figure 2:
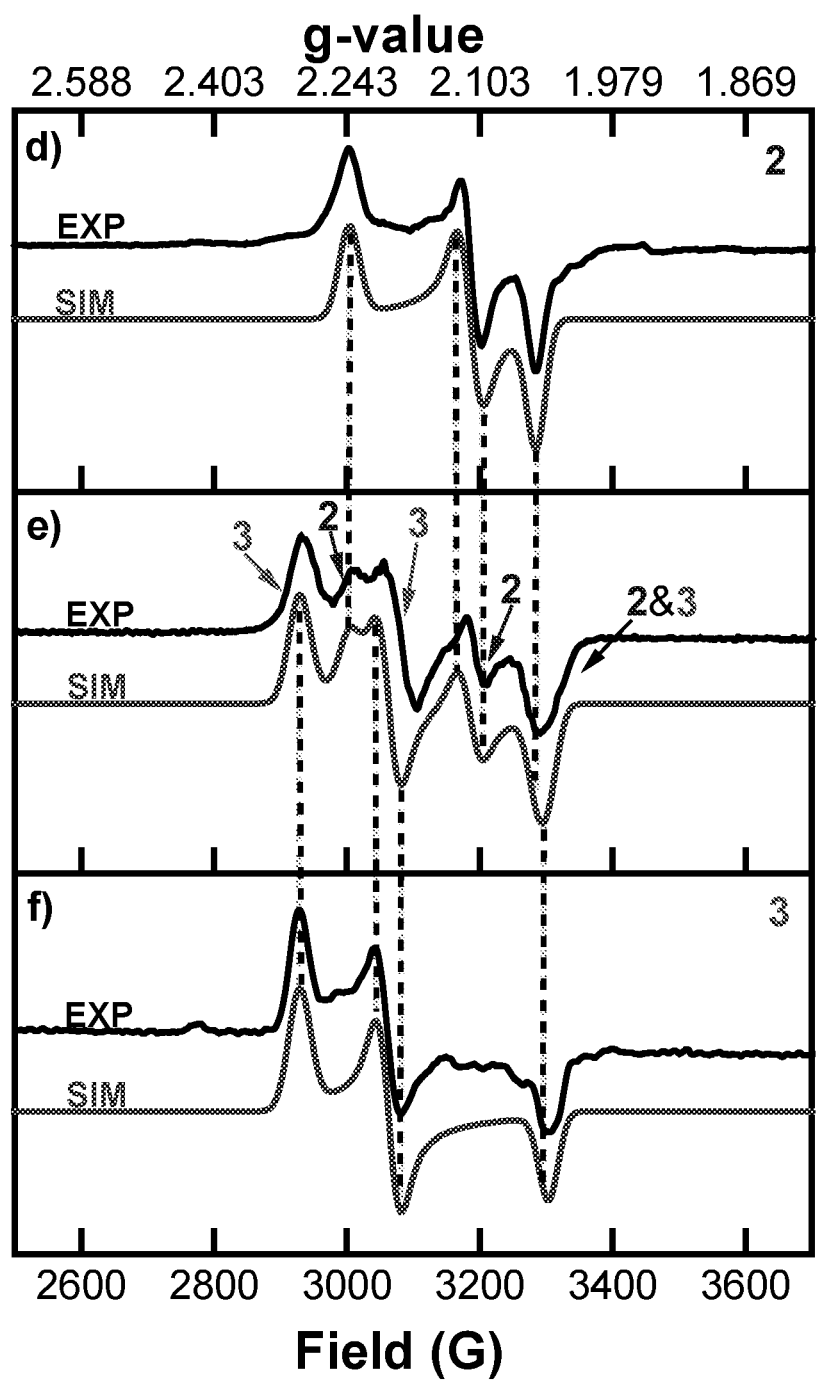
FIG. 2. Experimental setup for EPR detection of proposed Ni$^I$ and Ni$^{III}$ species (see Scheme 3). Experimental (top trace) and simulated (bottom trace) EPR spectra of the reaction mixtures recorded at 77 K in 1:5 MeOH:PrCN frozen glass: (d) 1b+CoCp*$_2$, (e) 1b+CoCp*$_2$+20 equiv 4-bromoacetophenone, (f) 1b+CoCp*$_2$+40 equiv 4-bromoacetophenone. The following parameters were used for simulation of (d) $g_x$=2.241, $g_y$=2.113, $g_z$=2.049; (f) $g_x$=2.298, $g_y$=2.197, $g_z$=2.037; (e) simulations of (d) and (f) were added in a 0.6:1 ratio.

Scheme 3.
(left) Experimental setup for EPR detection of proposed Ni$^I$ and Ni$^{III}$ species upon reduction of 1b and subsequent oxidative addition of aryl bromide (FIG 2).

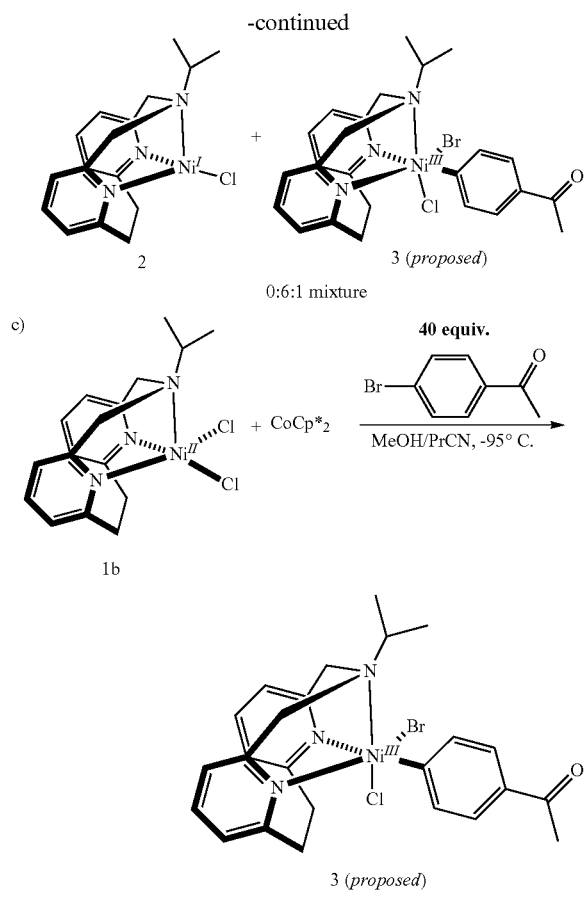

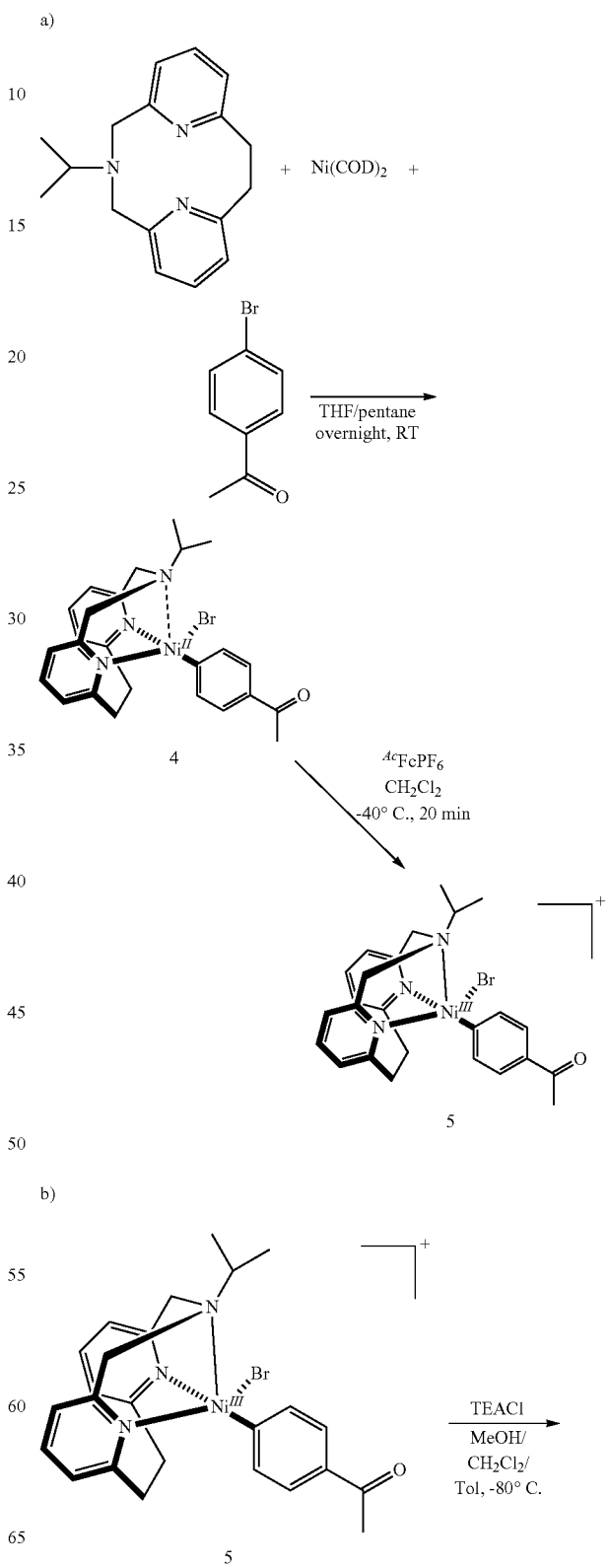

Figure 3:
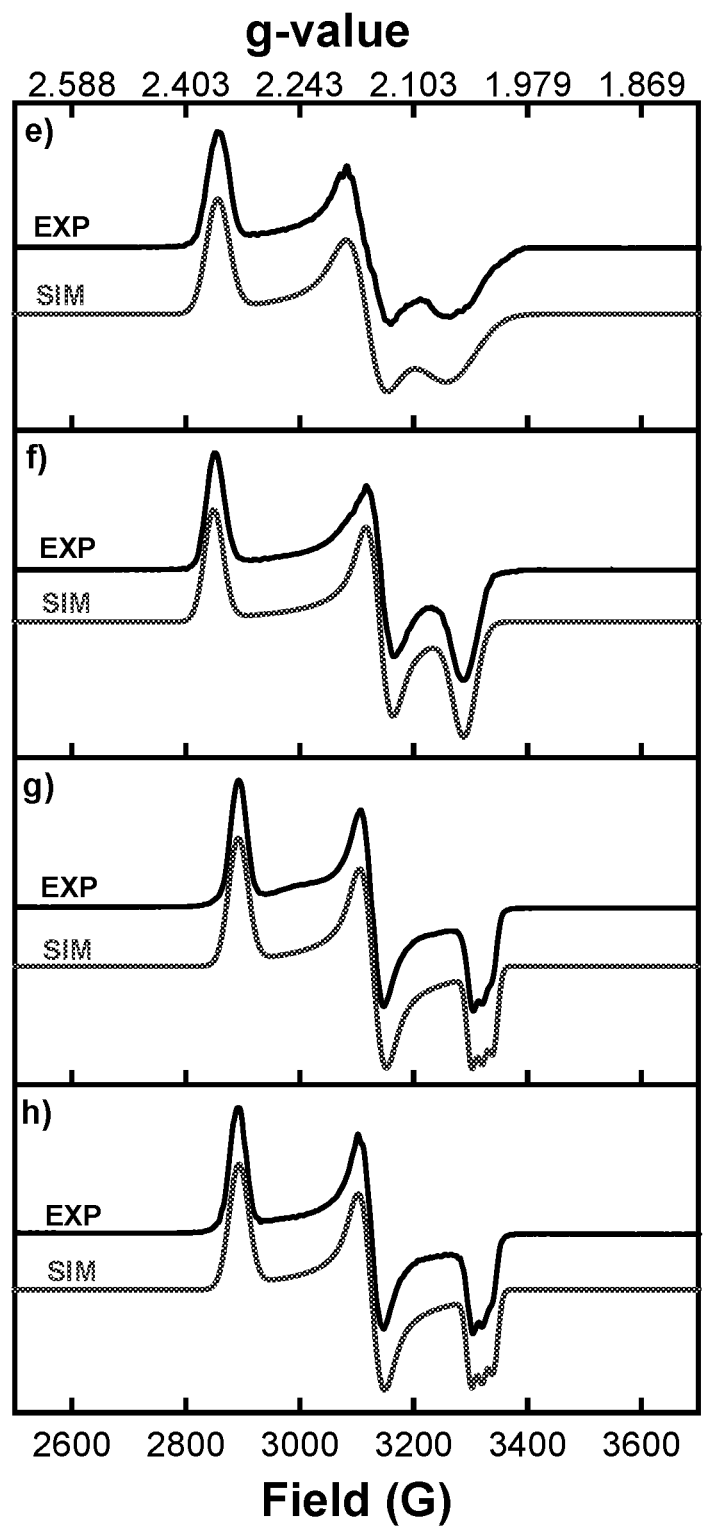
FIG. 3. Experimental setup for synthesis of ($^{iPr}$N3)Ni$^{II}$PhAcBr (4) and EPR detection of (a) ($^{iPr}$N3)Ni$^{III}$PhAcBr$^+$ (5), (b) ($^{iPr}$N3)Ni$^{III}$PhAcCl$^+$ (6), and (c and d) [($^{iPr}$N3)Ni$^{III}$(PhAc)OMe]$^+$ (7) (see Scheme 4). Experimental (top trace) and simulated (bottom trace) EPR spectra of the reaction mixtures recorded at 77 K in 1:1:3 MeOH:CH$_2$Cl$_2$:Toluene frozen glass: (e) [($^{iPr}$N3)Ni$^{III}$(PhAc)Br]$^+$ (5), (f) [($^{iPr}$N3)Ni$^{III}$(PhAc)Cl]$^+$ (6), and (g and h) [($^{iPr}$N3)Ni$^{III}$(PhAc)OMe]$^+$ (7). The following parameters were used for simulation of (e) $g_x$=2.356, $g_y$=2.158, $g_z$=2.059; (f) $g_x$=2.363, $g_y$=2.144, $g_z$=2.047; (g) $g_x$=2.326, $g_y$=2.151, $g_z$=2.027 ($A_z$(N)=19.4 G); (h) $g_x$=2.326, $g_y$=2.152, $g_z$=2.027 ($A_z$(N)=19.5 G).

Scheme 4. (left) Experimental setup for synthesis of ($^{iPr}$N3)Ni$^{II}$(PhAc)Br (4) and EPR detection of (a) [($^{iPr}$N3)Ni$^{III}$(PhAc)Br]$^+$ (5), (b) [($^{iPr}$N3)Ni$^{III}$(PhAc)Cl]$^+$ (6), and (c and d) [($^{iPr}$N3)Ni$^{III}$(PhAc)OMe]$^+$ (7) (FIG 3).

To further probe the role of various Ni$^{III}$ species in the C—O coupling reaction, we independently synthesized the ($^{iPr}$N3)Ni$^{II}$(PhAc)Br complex 4 via oxidative addition of 4-bromoacetophenone to Ni(COD)$_2$ in the presence of $^{iPr}$N3 (FIG. 3a). While 4 is unstable in solution at room temperature, rapidly decomposing to green ($^{iPr}$N3)Ni$^{II}$Br$_2$ complex, it is stable at −40° C. for several hours. The decomposition of a related nickel complex, (bpy)Ni$^{II}$PhBr, to (bpy)Ni$^{II}$Br$_2$ has been observed previously and proposed to proceed via a bimolecular pathway. The instability of 4 in solution prevented us from obtaining X-ray quality crystals, nonetheless since 4 is diamagnetic its structural evidence was provided by $^1$H NMR obtained at −40° C., which shows a slight peak broadening due to the flexible amine arm. Oxidation of 4 with acetylferrocenium hexafluorophosphate ($^{Ac}$FcPF$_6$) at −40° C. generated the Ni$^{III}$[($^{iPr}$N3)Ni$^{III}$(PhAc)Br]$^+$ complex 5 (FIG. 3a).

The effective magnetic moment μ$_{eff}$ of 1.98μ$_b$, determined using the Evans method, is consistent with a S=½ ground state for 5, as expected for a Ni$^{III}$ center. The rhombic EPR spectrum of 5 with g$_x$=2.356, g$_y$=2.158, g$_z$=2.059 is significantly different than that of 3 (FIG. 3e vs. FIG. 2f), solidifying the proposed 6-coordinate structure in FIG. 2c. Complex 5 was stable in solution at −35° C. and can be isolated as a red solid, yet it was recalcitrant to form single crystals. Therefore, the presence of a Ni$^{III}$ center was further confirmed by X-ray photoelectron spectroscopy (XPS), which shows an increase of the Ni 2$_{p3/2}$ and 2$_{p1/2}$ binding energies of ~1.5 eV for 5 versus 4, demonstrating the presence of a further oxidized Ni center.

c)

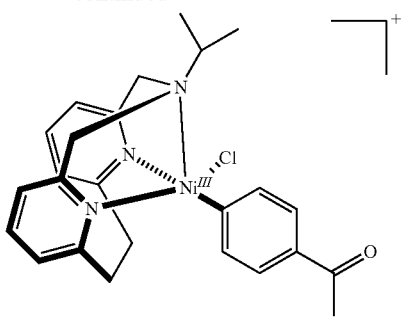

6

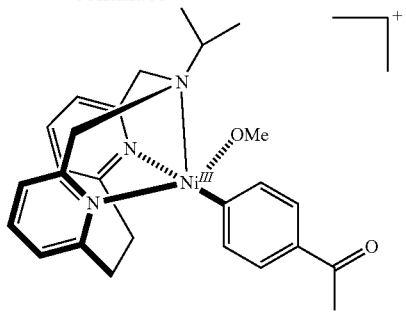

7

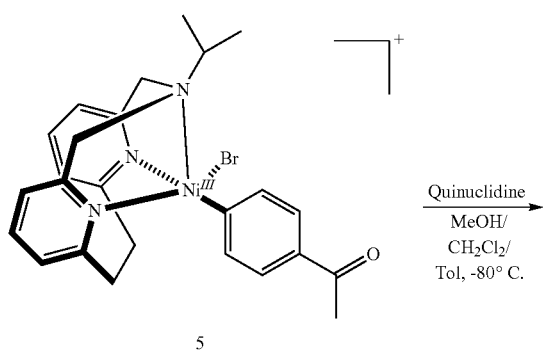

5

Quinuclidine
─────────→
MeOH/
CH₂Cl₂/
Tol, -80° C.

d)

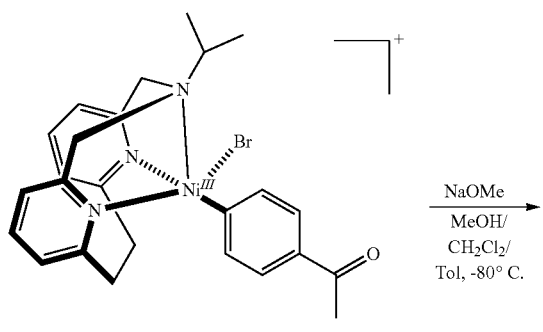

5

NaOMe
─────────→
MeOH/
CH₂Cl₂/
Tol, -80° C.

7

The stability of 5 allowed us to investigate its reactivity. When 5 was reacted with 1 equiv tetraethylammonium chloride (TEACl, FIG. 3b), a rhombic EPR spectrum with $g_x=2.363$, $g_y=2.144$, $g_z=2.047$ and sharper signals than the spectrum of 5 was obtained, indicating the likely formation of the [($^{iPr}$N3)Ni$^{III}$(PhAc)Cl]$^+$ species 6 (FIG. 3f vs. FIG. 3e). A similar EPR signal broadening due to superhyperfine coupling to the Br atom (I=3/2) vs the Cl atom (I=3/2) was observed in a previous study by our group, where the structural analysis of [($^{tBu}$N4)Ni$^{III}$ArX]$^+$ complexes (X=Br or Cl) confirmed the effect of the identity of the halide onto the EPR spectra. Importantly, an EPR spectrum resembling the proposed 6-coordinate species ($^{iPr}$N3)Ni$^{III}$(PhAc)BrCl (3) was not observed, supporting the instability of this sterically hindered species 3. GC-MS analysis of the solution of 6 after warming up to room temperature in the absence of MeOH reveals Ar—Cl product formation, while the reaction between ($^{iPr}$N3)Ni$^{II}$(PhAc)Br (4) and PhICl₂ generates an EPR spectrum identical to that of 6, providing additional experimental evidence for the halide exchange.

We next probed the important step of ligand exchange with an alkoxide group. The addition at −80° C. of quinuclidine in MeOH to 5 generated a species assigned as the Ni$^{III}$-aryl alkoxide complex [($^{iPr}$N3)Ni$^{III}$(PhAc)(OMe)]$^+$ (7), with a rhombic EPR signal with $g_x=2.326$, $g_y=2.151$, $g_z=2.027$ and superhyperfine coupling to the one axial N (I=1) donor in the $g_z$ direction of $A_z(N)=19.4$ G (FIG. 3g). We posit that replacement of the halides that exhibit superhyperfine interactions (Br or Cl, I=3/2) by the methoxide ligand may resolve the superhyperfine coupling to the N atom along the $g_z$ direction, while the weaker π-donor methoxide may also lead to a stronger Ni—N$_{axial}$ interaction. The identity of 7 was further confirmed by the treatment of 5 with 1 equiv NaOMe, which generated an identical EPR spectrum (FIG. 3h). Importantly, to the best of our knowledge this is the first experimental observation of a ligand exchange reaction (either by a halide or alkoxide) occurring at a Ni$^{III}$ metal center, which is typically proposed as a key step in Ni-mediated aryl halide transformations.

Upon warming up to room temperature, species 6 and 7 underwent C—O bond-forming reductive elimination, affording 4-methoxyacetophenone together with different amounts of acetophenone (Table 3), and consistent with a favorable reductive elimination from a Ni$^{III}$ species. Moreover, the addition of excess anionic ligands (Cl$^-$ or OMe$^-$) leads to increased yields of the C—O coupled product (Table 3) and faster decomposition of 6 and 7. We propose that coordination of an additional anionic ligand in the presence of excess base leads to the formation of a congested 6-coordinate Ni$^{III}$ center, due to the steric hindrance of the ethylene bridge that blocks the second axial coordination site (FIG. 5g), and consequently results in accelerated C—O reductive elimination. This is also in line with the rapid decay of the 6-coordinate species ($^{iPr}$N3)Ni$^{III}$(PhAc)BrCl (3) that was observed above (FIG. 2c and FIG. 11). In addition, the rapid reductive elimination from a 6-coordinate Ni$^{III}$ center may preclude β-hydride elimination (Table 3, entry 6), which is likely the source of the formation of b. Overall, these EPR and reactivity studies provide a complete picture of the Ni$^I$/Ni$^{III}$ catalytic cycle for the C—O cross-coupling reaction, with experimental evidence for each critical step in this process: oxidative addition, transmetalation/ligand exchange, and reductive elimination.

Figure 4:
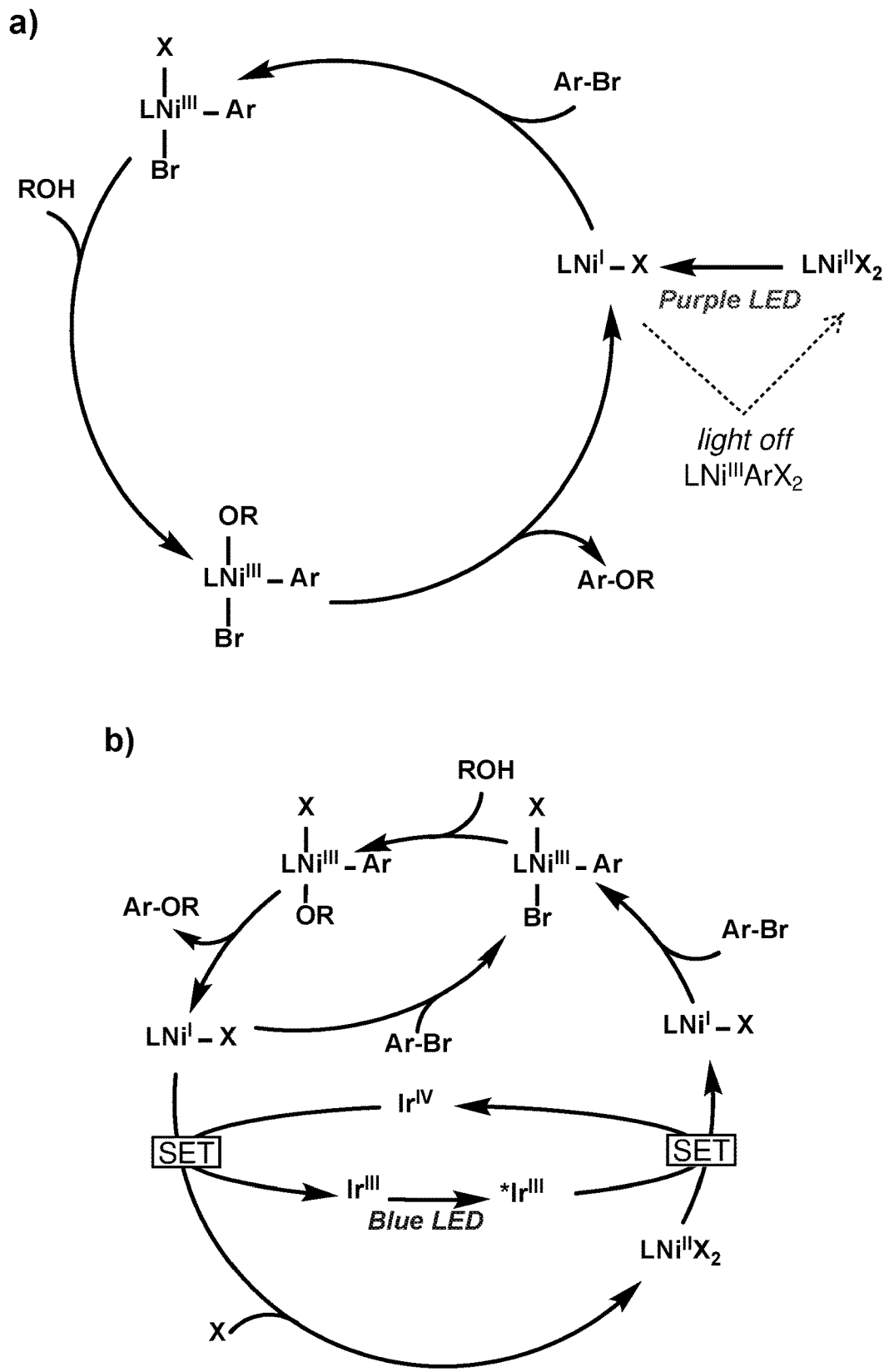
FIG. 4. Proposed mechanisms for the C—O cross coupling for (a) direct light-promoted Ni photocatalysis with purple LED light which operates by light-induced modulation of Ni oxidation states and (b) photoredox/Ni dual catalysis with blue LED light which operates by modulation of Ni oxidation state by photocatalyst. X=Cl or Br, L=$^{Me}$N3 or $^{iPr}$N3.

Mechanistic Considerations. Finally, based on the photoredox/Ni dual catalytic studies under blue LED light, we evaluated the thermodynamic feasibility of the photocatalytic process in the C—O coupling reaction. A comparison of the redox potentials of the Ni complexes and photocatalysts implies that a reductive quenching pathway is not operating, as the observed production yields contradicts the trend of the oxidation strength of excited photocatalysts (Example 5). Instead, and oxidative quenching pathway, where the initial step is the single-electron reduction of Ni$^{II}$ by the excited photocatalyst, is proposed to be operative, as this is in line with our results in which all photocatalysts with E(M$^+$/*M)<–0.87 V afforded the C—O coupling product. By combining the insights obtained from EPR and reactivity studies and the photoredox/Ni dual catalysis, two photocatalytic mechanisms are proposed (FIG. 4).

The ($^R$N3)Ni$^{II}$ complex is reduced to a Ni$^I$ species by irradiation with purple LED light or the excited photocatalyst, which undergoes an oxidative addition with aryl halide to form a transient ($^R$N3)Ni$^{III}$ArBrX species. This Ni$^{III}$ species can then undergo a ligand exchange with the alcohol substrate in presence of excess base to generate the ($^R$N3) Ni$^{III}$Ar(OR)X species, which is then proposed to undergo a subsequent reductive elimination to yield the C—O coupled product and regenerate a ($^R$N3)Ni$^I$ species, completing the catalytic cycle. Regeneration of photocatalyst can be achieved by a SET reaction between Ni$^I$ and the oxidized photocatalyst. Importantly, the use of the tridentate pyridinophane $^R$N3 ligands generate sterically hindered 6-coordinate Ni$^{III}$ centers due to the H atoms of the ethylene bridge and that are thus proposed to promote a rapid reductive elimination.

Conclusion. We herein report new tridentate pyridinophane $^R$N3 ligands and their Ni complexes, which were employed in photocatalytic C—O cross-coupling catalytic and mechanistic studies. The ($^R$N3)NiCl$_2$ complexes were active photocatalysts for the C—O cross-coupling in the absence of a precious-metal photocatalyst. Employing these newly developed $^R$N3 ligands allowed us to detect the critical but so far putative steps of the C—O cross-coupling catalytic cycle involving paramagnetic Ni species: the oxidative addition of an aryl halide to a Ni$^I$ species to generate a Ni$^{III}$ species, the ligand exchange/transmetalation step at a Ni$^{III}$ center, and the C—O bond forming reductive elimination from a Ni$^{III}$ species. The present work suggests that these $^R$N3 ligands can lead to the development of new Ni catalysts, and also are practical platform for detailed mechanistic studies of related Ni-catalyzed reactions.

TABLE 3

Stoichiometric reactivity of 5 with TEACl, quinuclidine, or NaOMe to yield the C—O coupled product through reductive elimination from Ni$^{III}$ intermediates.

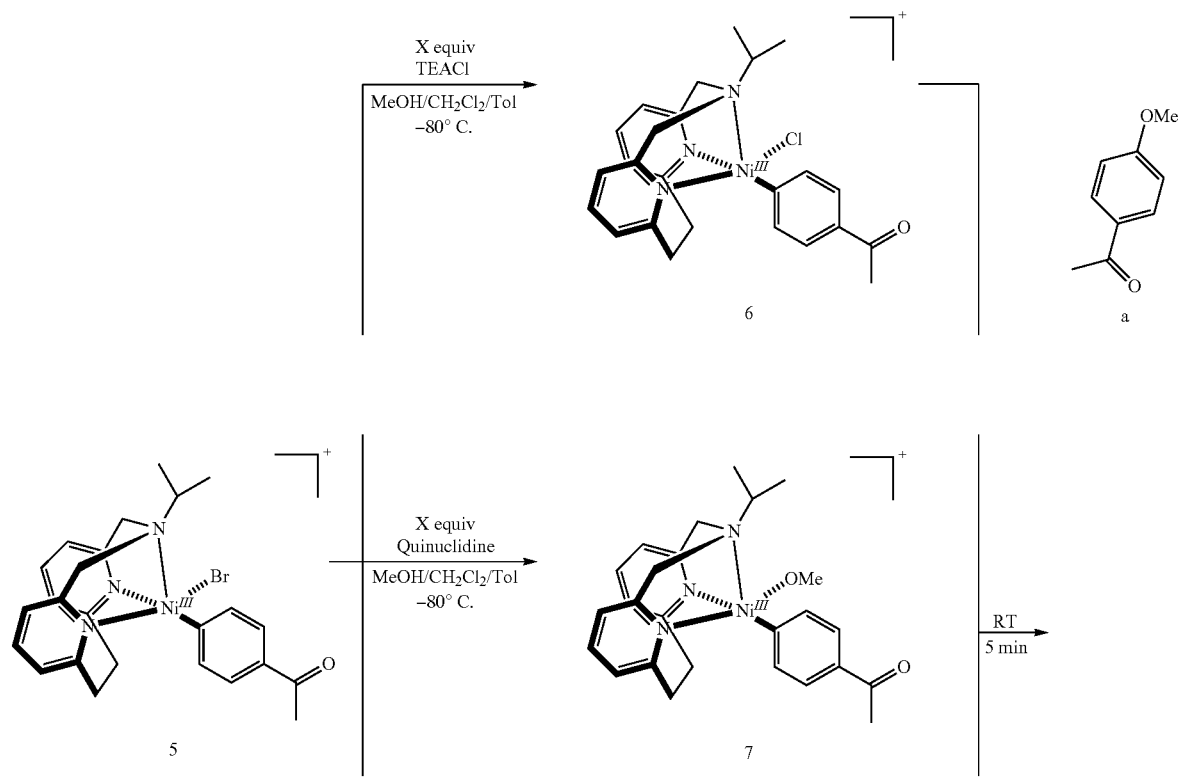

TABLE 3-continued

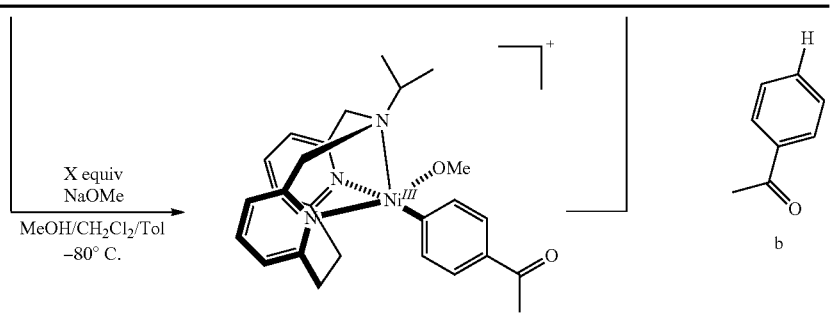

| Entry | Additive equiv. | a (%)[a] | b (%)[a] |
|---|---|---|---|
| 1 | 1 equiv. TEACl | 13 | 20 |
| 2 | 10 equiv. TEACl | 33 | 30 |
| 3 | 1 equiv. Quinuclidine | 28 | 28 |
| 4 | 10 equiv. Quinuclidine | 33 | 22 |
| 5 | 1 equiv. NaOMe | 41 | 24 |
| 6 | 10 equiv. NaOMe | 57 | 0 |

[a]Yields were determined using GC-FID with 1,3-benzodioxole as a standard.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Methods

General procedure for the C—O cross-coupling reaction. In a $N_2$-filled glovebox, 4-bromoacetophenone (0.4 mmol, 1.0 equiv), quinuclidine (0.44 mmol, 1.1 equiv), MeOH (1.6 mmol, 4 equiv), ($^{Me}$N3)NiCl$_2$ (2 mol %), and a magnetic stir bar were added into 0.4 mL THF in a vial. The vial was irradiated with one Kessil purple LED lamp ($\lambda_{max}$=390 nm, max 52 W) under fan cooling. After 24 h, 1,3-benzodioxole (0.4 mmol) was added to the reaction mixture at a standard, and the reaction mixture was analyzed by $^1$H NMR in CDCl$_3$ and GC-FID to determine the yield of C—O coupled product. Authentic 4-methoxyacetophenone was purchased from AK scientific and used to determine the retention time and response factor for GC-FID quantification.

General procedure for EPR detection of 2 and 3: In $N_2$-filled glovebox, a MeOH solution of 1b was layered on top of a frozen PrCN solution of CoCp*$_2$ and 4-bromoacetophenone in the EPR tube. The mixture was quickly frozen and taken outside of the glove box. The reaction mixture was mixed at −95° C., quickly frozen at 77 K, and then the sample was warmed up for ~10 s to −95° C. to allow for a complete reaction.

General procedure for EPR detection of 5, 6, and 7: In $N_2$-filled glovebox, an EPR tube was charged with 1:3 CH$_2$Cl$_2$:Toluene or PrCN solution of 5 and frozen at 77 K. A MeOH solution of TEACl, quinuclidine, or NaOMe was added over the frozen solution of 5. After taking out the EPR tube from the glovebox, an initial EPR spectrum was taken at 77 K (for 5). After a quick shake of the tube for 10 s at −95° C. (for 6 or 7), the sample was frozen at 77 K.

Data availability. Crystallographic data for the structures reported in this article have been deposited at the Cambridge Crystallographic Data Centre, under deposition numbers CCDC 2085516 (1a) and 2085517 (1b).

Example 2. Synthesis of Ligands and Catalysts

Physical Methods. $^1$H and $^{13}$C NMR spectra were recorded using a Bruker 400 MHz or 500 MHz spectrometer. UV-vis absorption spectra were recorded in CH$_2$Cl$_2$ in 1 cm quartz cuvettes using a Varian Cary 60 spectrophotometer. EPR spectra were recorded on a Bruker 10" EMXPlus X-band Continuous Wave EPR spectrometer at 77 K. EPR spectra simulation and analysis were performed using Bruker WINEPR SimFonia program, version 1.25. The spin state of Ni$^{III}$ complex was determined using $^1$H NMR method of Evans at −40° C. Elemental analysis was carried out by the Microanalysis Laboratory at University of Illinois at Urbana-Champaign (UIUC) using an Exeter Analytical-Model CE440 CHN Analyzer. Cyclic voltammetry (CV) experiments were performed with a CHI 660D Electrochemical Analyzer using a three-electrode system in a nitrogen-filled glove box. A 3 mm diameter glassy-carbon electrode, Pt wire, and silver wire were used as working electrode, counter electrode, and pseudoreference electrode, respectively. Measurements were carried out in acetonitrile or dichloromethane solution with 0.1 M TBAPF$_6$ as a supporting electrolyte at a scan rate of 0.1 V/s. Ferrocene was used as an internal standard, and potentials were referenced to the ferrocene/ferrocenium couple. The X-ray Photoelectron Spectroscopy (XPS) experiments were performed at the Materials Research Laboratory at UIUC using Kratos Axis ULTRA X-ray Photoelectron Spectrometer. Photocatalysis experiments were carried out using one Kessil lamp model PR160 blue LED ($\lambda_{max}$=456 nm, max 50 W) or purple LED ($\lambda_{max}$=390 nm, max 52 W).

Reactions were performed in ambient conditions unless otherwise stated. Solvents were purified prior to use by passing through a column of activated alumina using an MBraun solvent purification system. All starting materials and reagents, unless otherwise specified, were obtained from commercial sources and used without further purification.

The starting material N-(tosyl)-2,11-diaza[3,3](2,6)pyridinophane ($^{TsH}$N4) was synthesized following our published procedure (Wessel, A. J.; Schultz, J. W.; Tang, F.; Duan, H.; Mirica, L. M., Improved synthesis of symmetrically & asymmetrically N-substituted pyridinophane derivatives. *Org. Biomol. Chem.* 2017, 15, 9923-9931).

Refer to Scheme 2 for the following synthetic steps:

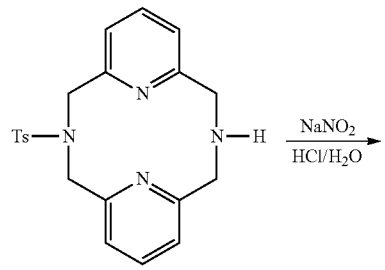

Synthesis of $^{TsNO}$N4 compound. A cold solution of NaNO$_2$ 270 mg in 3 mL of water was added to a solution of $^{TsH}$N4 100 mg in 2 mL of conc. HCl. The mixture was left overnight at room temperature. Next day, the yellowish white solids were filtered and washed with Et$_2$O. Pale-yellow or white solid product were collected and dried. Yield: $^{TsNO}$N$_4$ (83 mg, 77%) $^1$H NMR (500 MHz, DMSO-d$_6$) δ 8.40 (t, J=7.8 Hz, 1H), 8.27 (t, J=7.8 Hz, 1H), 8.00 (d, J=7.8 Hz, 1H), 7.85 (d, J=7.8 Hz, 1H), 7.81-7.73 (m, 4H), 7.45 (d, J=8.0 Hz, 2H), 6.14 (s, 2H), 5.22 (s, 2H), 4.93 (s, 2H), 4.84 (s, 2H), 2.43 (s, 3H).

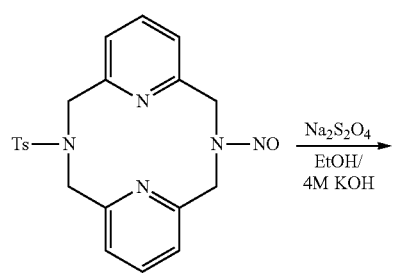

N-nitroso reduction reaction. Under N$_2$, the $^{TsNO}$N4 compound (60 mg) was dissolved into a mixture of 4 M KOH 5 mL and ethanol 5 mL and heated under reflux (100-110° C.). After stirring for 1 h, the reaction mixture was cooled down to room temperature. Then solid sodium hydrosulfite (88 mg) was quickly added to the reaction mixture, and the reaction mixture was refluxed at 110° C. for 3 h. Then the mixture was cooled down and poured into 40 mL of water. The resulting solution was extracted with CH$_2$Cl$_2$ (3×25 mL). The combined organic layers were dried over MgSO$_4$ and filtered. The clear solution was concentrated to dryness to give a white solid or yellowish white solid. Yield: $^{Ts}$N3 (34 mg, 63%) $^1$H NMR (400 MHz, Chloroform-d) δ 7.86-7.76 (m, 2H), 7.51 (t, J=7.5 Hz, 2H), 7.35 (d, J=8.0 Hz, 2H), 7.10 (d, J=7.6 Hz, 2H), 6.95 (d, J=7.6 Hz, 2H), 4.36 (s, 4H), 2.98 (s, 4H), 2.47 (s, 3H). $^{13}$C NMR (126 MHz, CDCl$_3$) δ 160.45, 153.37, 143.62, 137.42, 130.24, 130.03, 127.51, 127.24, 122.50, 121.77, 54.24, 39.35, 21.84. HRMS-ESI (m/z): [M+H]$^+$ calcd for C$_{21}$H$_{12}$N$_3$O$_2$S, 380.1433; found 380.1440.

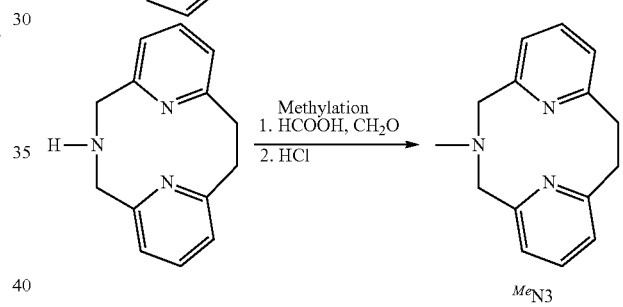

Synthesis of $^{Me}$N3 ligand. Detosylation: Under N$_2$, $^{Ts}$N3 300 mg was dissolved in 15 mL of 90% sulfuric acid. This mixture was stirred and refluxed at 110° C. for 2.5 hr. After cooling, the solution was basified with saturated KOH solution. The resulting solution was extracted with CH$_2$Cl$_2$, the organic layer was dried over anhydrous K$_2$CO$_3$ and MgSO$_4$. The filtrate was dried to give an off-white solid. Yield: $^H$N3 (130 mg, 73%) $^1$H NMR (400 MHz, Chloroform-d) δ 7.54 (t, J=7.5 Hz, 2H), 7.02 (dd, J=17.6, 7.6 Hz, 4H), 3.87 (s, 4H), 3.01 (s, 4H).

Methylation: Under N$_2$, $^H$N3 17 mg was dissolved in formic acid 2.5 mL and 40% formaldehyde solution 0.25 mL. The mixture was stirred and refluxed at 110° C. for overnight. After cooling the solution was treated with concentrated HCl 0.25 mL. After several minutes the solution was dried, and the residue was basified with NaOH solution and extracted with CH$_2$Cl$_2$. The organic layer was dried over anhydrous K$_2$CO$_3$ and MgSO$_4$. The filtrate was dried to give slightly yellowish-white solid. Yield: $^{Me}$N3 (17 mg, 94%) $^1$H NMR (400 MHz, Chloroform-d) δ 7.59 (t, J=7.6 Hz, 2H), 7.17-7.08 (m, 4H), 3.69 (s, 4H), 3.00 (s, 4H), 2.76 (s, 3H). $^{13}$C NMR (126 MHz, Chloroform-d) δ 160.26, 156.20, 136.95, 121.76, 120.95, 62.70, 62.67, 62.64, 47.23, 47.20, 47.18, 39.49. HRMS-ESI (m/z): [M+H]$^+$ calcd for C$_{15}$H$_{17}$N$_3$, 240.1501; found, 240.1492.

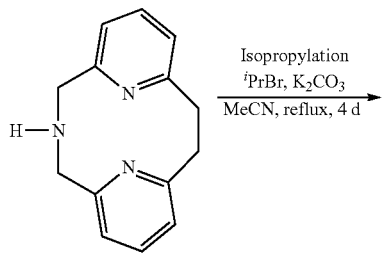

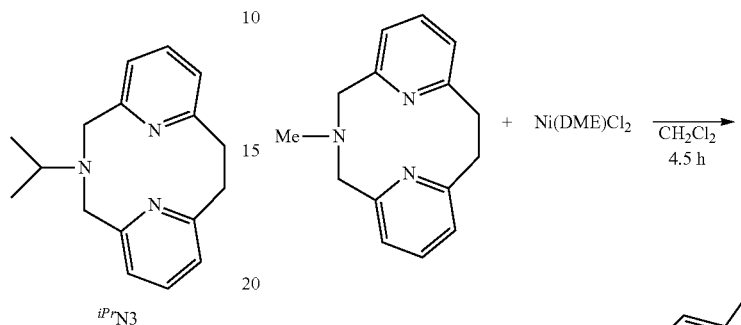

Synthesis of $^{iPr}$N3 ligand. Isopropylation: $^{H}$N3 (390 mg, 1.73 mmol), isopropylbromide (8.1 mL, 86.5 mmol, 50 equiv), anhydrous K$_2$CO$_3$ (2.87 g, 20.7 mmol, 12 equiv), and dry MeCN (60 mL) were charged into a 200 mL Schlenk flask with a magnetic stir bar. The reaction mixture was refluxed under N$_2$ for 4 days. The solution was then cooled to room temperature, and the solvent was removed under reduced pressure. The residue was suspended in 100 mL of CH$_2$Cl$_2$ and then washed with 1M NaOH. The CH$_2$Cl$_2$ layer was isolated, and dried over MgSO$_4$, evaporated and further dried under vacuum to give a pale yellow solid. Yield: $^{iPr}$N3 (416 mg, 90%) $^1$H NMR (500 MHz, Chloroform-d) δ 7.51 (t, J=7.6 Hz, 2H), 7.03 (ddd, J=24.0, 7.6, 1.0 Hz, 4H), 3.74 (s, 4H), 3.23-3.18 (m, 1H), 3.00 (s, 4H), 1.26 (s, 6H). $^{13}$C NMR (126 MHz, Chloroform-d) δ 159.98, 157.96, 136.87, 121.53, 121.29, 57.32, 56.27, 39.09, 19.96. HRMS-ESI (m/z): [M+H]$^+$ calcd for C$_{17}$H$_{21}$N$_3$, 268.1814; found 268.1812 of CH$_2$Cl$_2$ at room temperature. The yellow mixture was stirred for 4.5 h and the yellow color was slowly turned to violet color. After 4.5 h, 10 mL of pentane was added, the precipitate was collected and dried under vacuum to afford violet solids. Yield: 34 mg, 45%. X-ray quality crystals were obtained by layering pentane and CH$_2$Cl$_2$ solution of the compound at −35° C.

Synthesis of ($^{Me}$N3)NiCl$_2$ (1b). Inside of glovebox, Ni(DME)Cl$_2$ (29 mg) and $^{Me}$N3 (32 mg) were dissolved in 10 ml of CH$_2$Cl$_2$ at room temperature. The yellow mixture was stirred for 4.5 h, slowly generating green precipitate. After 4.5 h, precipitate was collected and dried under vacuum to afford highly insoluble green solids. Yield: 44 mg, 91%. Insolubility of this product prevents spectroscopic characterization. X-ray quality crystals were obtained by layering pentane and MeOH solution of the compound at −35° C.

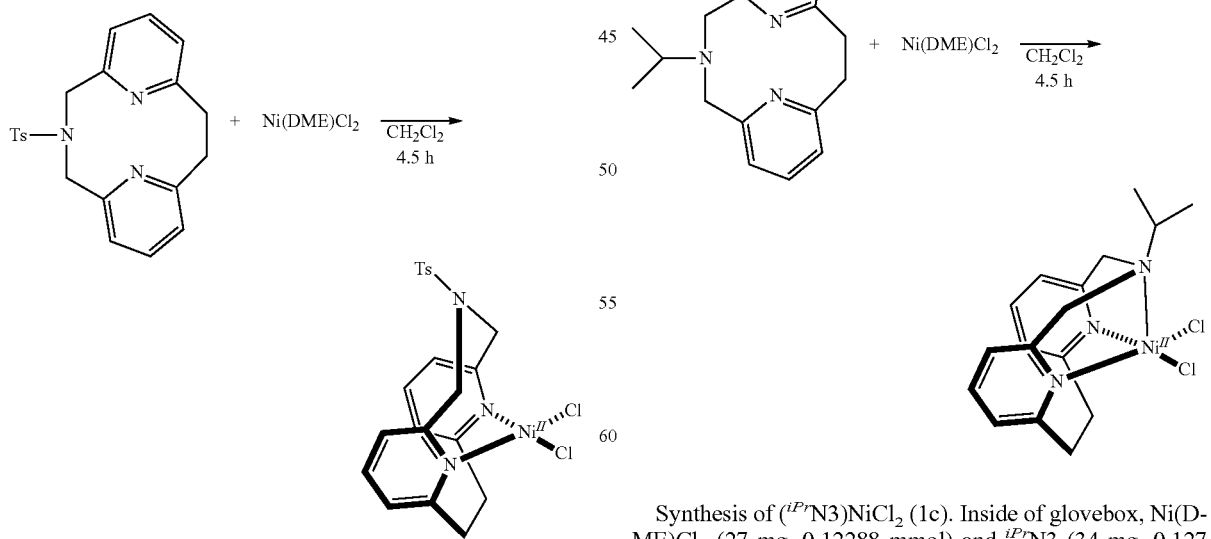

Synthesis of ($^{Ts}$N3)NiCl$_2$ (1a). Inside of glovebox, Ni(DME)Cl$_2$ (34 mg) and $^{Ts}$N3 (19 mg) were dissolved in 10 mL Synthesis of ($^{iPr}$N3)NiCl$_2$ (1c). Inside of glovebox, Ni(DME)Cl$_2$ (27 mg, 0.12288 mmol) and $^{iPr}$N3 (34 mg, 0.127 mmol) were dissolved in 10 mL of CH$_2$Cl$_2$ at room temperature. The yellow mixture was stirred for 4.5 h and yellow color was slowly turned to green color. After 4.5 h, green precipitate was collected and dried under vacuum to afford bright green solids. Yield: 47 mg, 96.9%. X-ray quality crystals were obtained by layering MeOH and CH$_2$Cl$_2$ solution of the compound at room temperature. $^1$H NMR (500 MHz, CD$_3$OD) δ 68.82, 54.57, 42.18, 13.45. Elemental analysis: Found: C, 43.76, H, 4.77, N, 8.61%; calculated C$_{17}$H$_{21}$Cl$_2$N$_3$Ni·1.2CH$_2$Cl$_2$: C, 43.82, H, 4.73, N, 8.42%

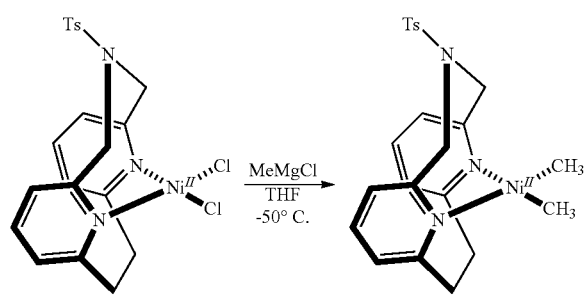

Synthesis of ($^{Ts}$N3)NiMe$_2$ (2a). To a stirred suspension of purple $^{Ts}$N3NiCl$_2$ (55 mg) in THF at −50° C., 2 equiv of MeMgCl (80 μL) in THF solution was added. The mixture was stirred and slowly warmed up to room temperature over 3-4 h. The resulting red solution was completely dried and the residue was extracted with toluene. The resulting toluene solution was filtered through celite to remove black solids twice and the red filtrate was dried under vacuum to give an orange-red solid. Yield: $^{Ts}$N3NiCl$_2$ (28 mg, 55%) $^1$H NMR (500 MHz, Benzene-d$_6$) δ 7.69 (d, J=7.9 Hz, 2H), 7.22 (d, J=14.0 Hz, 2H), 7.06 (d, J=7.7 Hz, 2H), 6.84 (d, J=7.8 Hz, 2H), 6.51 (t, J=7.7 Hz, 2H), 6.09 (d, J=7.6 Hz, 2H), 5.24-5.07 (m, 2H), 4.93 (d, J=14.2 Hz, 2H), 2.87-2.68 (m, 2H), 1.97 (s, 3H), −0.01 (s, 6H).

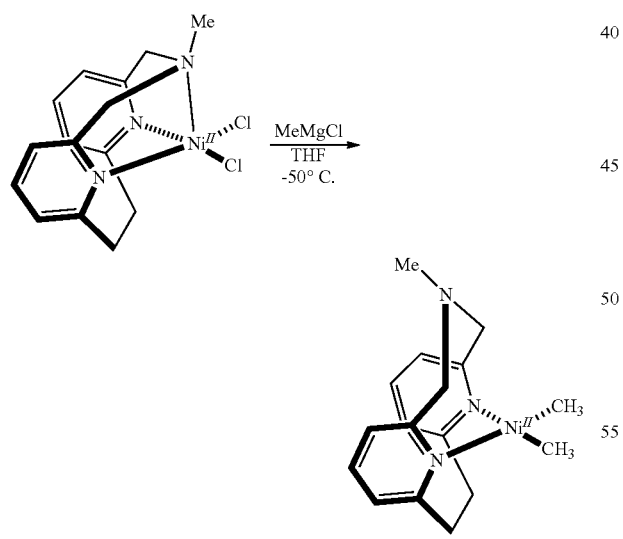

Synthesis of ($^{Me}$N3)NiMe$_2$ (2b). To a stirred suspension of purple $^{Me}$N3NiCl$_2$ (48 mg) in THF at −50° C., 2 equiv of MeMgCl (90 μL) in THF solution was added. The mixture was stirred and slowly warmed up to room temperature over 3-4 h. The resulting red solution was completely dried and the residue was extracted with toluene. Resulting toluene solution was filtered through celite twice and filtrate was dried to give orange-red solid. Yield: $^{Ts}$N3NiCl$_2$ (19 mg, 44%) $^1$H NMR (500 MHz, Benzene-d$_6$) δ 7.24 (d, J=14.0 Hz, 2H), 6.42 (t, J=7.6 Hz, 2H), 6.08 (d, J=7.6 Hz, 2H), 5.98 (d, J=7.6 Hz, 2H), 5.22 (d, J=9.4 Hz, 2H), 3.85 (d, J=14.0 Hz, 2H), 2.76 (d, J=9.7 Hz, 2H), 1.66 (s, 3H), 0.13 (d, J=1.5 Hz, 6H). $^{13}$C NMR (126 MHz, Benzene-d$_6$) δ 158.82, 156.76, 133.70, 122.07, 122.00, 62.72, 38.15, 33.56, −12.06.

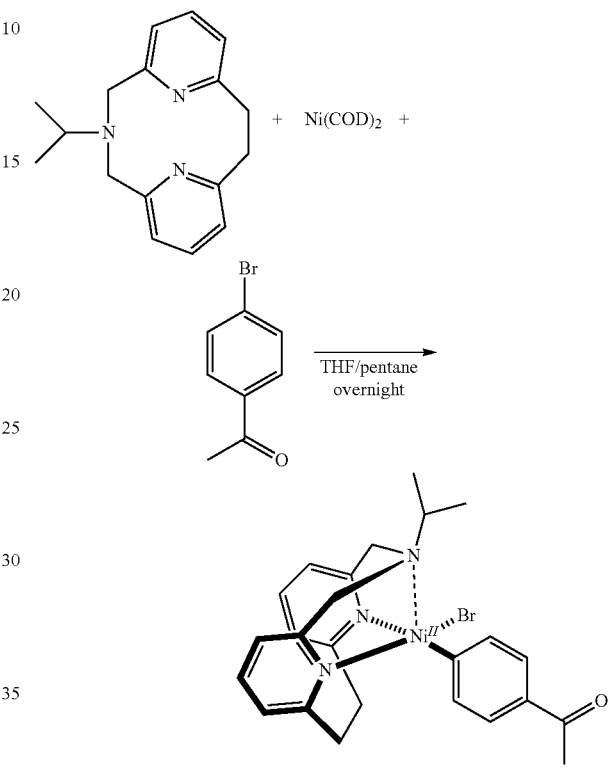

Synthesis of ($^{iPr}$N3)Ni(PhAc)Br (4). Inside of glovebox, Ni(COD)$_2$ (48 mg, 0.17 mmol), 4-bromoacetophenone (35 mg, mmol) and $^{iPr}$N3 (47 mg, 0.18 mmol) were dissolved in 3 mL of THF at room temperature. After 10 min, 2 mL of Pentane was added. The mixture was stirred for overnight and brick red precipitate was collected and dried under vacuum. Yield: 52 mg, 58%. $^1$H NMR (500 MHz, CD$_2$Cl$_2$, −40° C.) δ 8.01-7.96 (m, 1H), 7.36 (d, J=6.9 Hz, 1H), 7.30 (d, J=8.0 Hz, 1H), 7.25 (t, J=7.5 Hz, 1H), 7.13 (d, J=7.9 Hz, 1H), 6.99 (d, J=7.5 Hz, 1H), 6.93 (d, J=8.0 Hz, 1H), 6.79 (d, J=7.7 Hz, 1H), 6.34 (s, 1H), 5.96 (s, 1H), 5.05 (d, J=16.6 Hz, 1H), 4.51 (d, J=12.8 Hz, 2H), 4.39 (t, J=16.1 Hz, 2H), 3.94 (d, J=14.1 Hz, 1H), 3.86 (d, J=12.5 Hz, 1H), 2.39 (s, 3H), 2.06 (d, J=5.6 Hz, 3H), 1.54 (d, J=5.7 Hz, 3H).

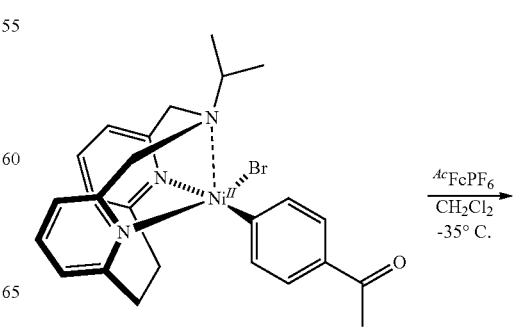

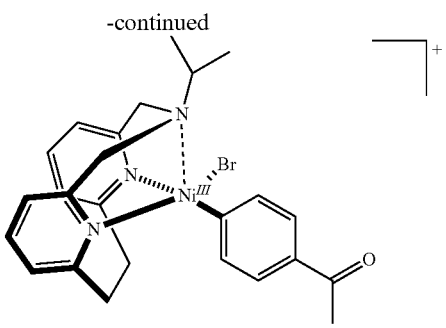

Synthesis of [($^{iPr}$N3)Ni$^{III}$(PhAc)(Br)]$^+$ (5). 10 mL dichloromethane solution of one equivalent acetylferrocenium hexafluorophosphate ($^{Ac}$FcPF$_6$, 22 mg, 0.059 mmol) was added to solids of ($^{iPr}$N3)Ni(PhAc)Br (31 mg, 0.059 mmol) at −35° C. and the resulting solution was stirred for 20 min. The volume of the solution was reduced to 5 mL and 10 mL of diethyl ether was added to precipitate the solids. The pink precipitated was filtered and washed with diethyl ether, and dried under vacuum. Yield: 32 mg, 81%. Evans method (CH$_2$Cl$_2$): $\mu_{eff}$=1.98$\mu_b$. Elemental analysis: Found: C, 43.35, H, 4.31, N, 7.06%; calculated C$_{25}$H$_{28}$BrF$_6$N$_3$NiOP: C, 44.81, H, 4.21, N, 6.27% Several attempts to obtain elemental analysis data proved unsuccessful, likely due to its decomposition during handling. Although these results are slightly outside the range viewed as establishing analytical purity, they are provided to illustrate the best values obtained to date.

Example 3. Nickel Catalyzed C—O Coupling Experiments

Scheme 5. Direct light-promoted Ni photocatalysis with Purple LED.

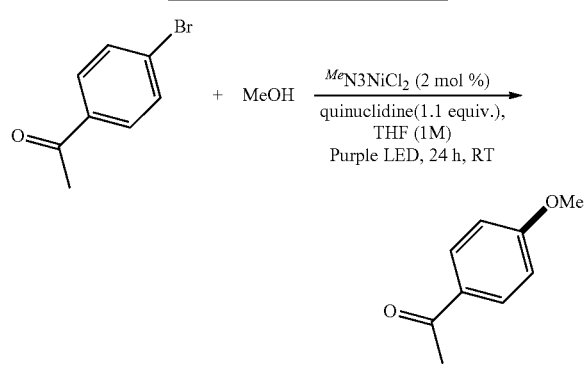

General procedure for the etherification reaction: In a nitrogen-filled glovebox, 4-Bromoacetophenone (0.4 mmol, 1.0 equiv.), quinuclidine (0.44 mmol, 1.1 equiv.), MeOH (1.6 mmol, 4 equiv.), ($^{Me}$N3)NiCl$_2$ (2 mol %), and a magnetic stir bar were added into 0.4 mL of THF in a vial. The vial was irradiated with one Kessil Purple LED ($\lambda_{max}$=390 nm, max 52 W) under fan cooling. After 24 h, 1,3-benzodioxole (0.4 mmol) was added to the reaction mixture. The residue was analyzed by $^1$H NMR in CDCl$_3$ and GC-FID to give the yield of the reaction. The authentic product 4-Methoxyacetophenone was purchased from AK scientific and used to determine retention time and a response factor for GC-FID quantification.

TABLE 4

Reaction optimization tables and control experiments.

| Control experiment | | | |
|---|---|---|---|
| Entry | Condition | Ni loading | Yield (%) |
| 1 | 1M, no light[a] | 2% | 0 |
| 2 | 1M | 0% | 0 |
| 3 | 1M, no Base | 2% | 0 |
| 4 | 1M, Blue LED instead Purple LED | 2% | 0 |

[a]The dark entry was covered with foil and placed under Purple LED.

| Concentration dependence | | | |
|---|---|---|---|
| Entry | Concentration | Ni loading | Yield (%) |
| 1 | 0.5M | 1% | 77 |
| 2 | 1M | 1% | 94 |
| 3 | 2M | 1% | 92 |
| 4 | 0.25M | 2% | 63 |
| 5 | 0.5M | 2% | 72 |
| 6 | 1M | 2% | 95 |

| Ni catalyst loading | | |
|---|---|---|
| Entry | Ni catalyst loading (1M) | Yield (%) |
| 1 | 0.2 mol % | 90 |
| 2 | 0.65 mol % | 90 |
| 3 | 1 mol % | 94 |
| 4 | 2 mol % | 95 |

| Solvent screening | | | |
|---|---|---|---|
| Entry | Solvent | Ni loading | Yield (%) |
| 1 | THF | 2% | 95 |
| 2 | MeCN | 2% | 20 |
| 3 | Toluene | 2% | 59 |

| Base screening | | |
|---|---|---|
| Entry | Base | Yield (%) |
| 1 | Quinuclidine | 95 |
| 2 | DABCO | 77 |
| 3 | DABCO, 36 h | 97 |
| 4 | DBU | 9.0 |
| 5 | K$_2$CO$_3$ | 0 |
| 6 | KH$_2$PO$_4$ | 0 |
| 7 | K$_3$PO4 | 0 |
| 8 | 10% quinuclidine + 1 equiv K$_2$CO$_3$ | trace (0.3) |

| Ni catalyst[a] | | |
|---|---|---|
| Entry | Ni source | Yield (%) |
| 1 | ($^{Me}$N3)NiCl$_2$ | 95 |
| 2 | ($^{Me}$N3)NiBr$_2$ | 90 |
| 3 | ($^{iPr}$N3)NiCl$_2$ | 82 |
| 4 | $^{Me}$N3 + Ni(DME)Cl$_2$ | 77 |
| 5 | [($^{iPr}$N3)Ni$^{III}$(PhAc)Br]PF$_6$ | 31 |
| 6 | ($^{Me}$N4)NiCl$_2$ | 2 |
| 7 | (iPr$_3$TACN)NiCl$_2$ | 51 |

[a]General reaction condition (1M in THF, Ni catalyst 2 wt %) was used.

| Alcohol scope | | |
|---|---|---|
| Entry | Alcohol | Yield (%) |
| 1 | MeOH | 95 |
| 2 | 1-hexanol | 90 |
| 3 | Benzyl alcohol | 86 |

Scheme 6. Photoredox/Ni dual catalysis with Blue LED.

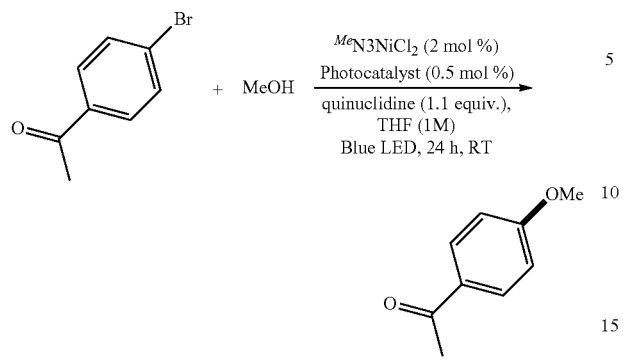

General procedure for the etherification reaction: In a nitrogen-filled glovebox, 4-Bromoacetophenone (0.4 mmol, 1.0 equiv.), quinuclidine (0.44 mmol, 1.1 equiv.), MeOH (1.6 mmol, 4 equiv.), ($^{Me}$N3)NiCl$_2$ (2 mol %), photocatalyst (0.5 mol %) and a magnetic stir bar were added into 0.4 mL of THF in a vial. The vial was irradiated with one Kessil Blue LED ($\lambda_{max}$=456 nm, max 52 W) under fan cooling. After 24 h, 1,3-benzodioxole (0.4 mmol) was added to the reaction mixture. The residue was analyzed by $^1$H NMR in CDCl$_3$ and GC-FID to give the yield of the reaction. The authentic product 4-Methoxyacetophenone was purchased from AK scientific and used to determine retention time and a response factor for GC-FID quantification.

TABLE 5

Photocatalyst screening.

| Entry | Photocatalyst | Yield (%) |
|---|---|---|
| 1 | no photocatalyst | 0 |
| 2 | [Ir(dF(CF$_3$)$_2$ppy)(dtbbpy)]PF$_6$ | 86 |
| 3 | Ir(ppy)$_3$ | 90 |
| 4 | [Ir(ppy)$_2$(dtbbpy)]PF$_6$ | 98 |
| 5 | [Ru(phen)$_3$]Cl$_2$ | trace (0.9) |
| 6 | [Ru(bpz)$_3$](PF$_6$)2 | 0 |

Example 4. Optimization of Nickel Catalyzed C—O Coupling Reactions (Table 6-12)

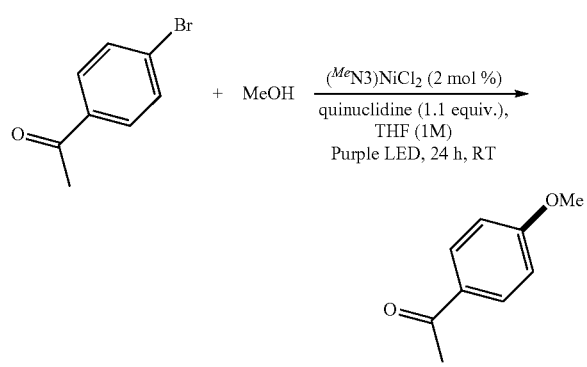

General procedure for the etherification reaction: In a nitrogen-filled glovebox, 4-bromoacetophenone (0.4 mmol, 1.0 equiv.), quinuclidine (0.44 mmol, 1.1 equiv.), MeOH (1.6 mmol, 4 equiv.), ($^{Me}$N3)NiCl$_2$ (2 mol %), and a magnetic stir bar were added into 0.4 mL of THF in a vial. The vial was irradiated with one Kessil purple LED ($\lambda_{max}$=390 nm, max 52 W) under fan cooling. After 24 h, 1,3-benzodioxole (0.4 mmol) was added to the reaction mixture. The residue was analyzed by 1H NMR in CDCl$_3$ and GC-FID to give the yield of the reaction. The authentic product 4-Methoxyacetophenone was purchased from AK scientific and used to determine retention time and a response factor for GC-FID quantification.

TABLE 6

Control experiment.

| Entry | Condition | Ni loading | Yield (%) |
|---|---|---|---|
| 1 | 1M, no light[a] | 2% | 0 |
| 2 | 1M | 0% | 0 |
| 3 | 1M, no Base | 2% | 0 |

[a]The dark entry was covered with foil and placed under purple LED.

TABLE 7

Concentration dependence.

| Entry | Concentration | Ni loading | Yield (%) |
|---|---|---|---|
| 1 | 0.5M | 1% | 77 |
| 2 | 1M | 1% | 94 |
| 3 | 2M | 1% | 92 |
| 3 | 0.25M | 2% | 63 |
| 4 | 0.5M | 2% | 72 |
| 5 | 1M | 2% | 95 |

TABLE 8

Ni catalyst loading.

| Entry | Ni catalyst loading (1M) | Yield (%) |
|---|---|---|
| 1 | 0.2 mol % | 90. ± 1[a] |
| 2 | 0.65 mol % | 90 |
| 3 | 1 mol % | 94 |
| 4 | 2 mol % | 95 ± 1[a] |

[a]The average product yield from three independent experiments

TABLE 9

Solvent screening.

| Entry | Solvent | Ni loading | Yield (%) |
|---|---|---|---|
| 1 | THF | 2% | 95 ± 1[a] |
| 2 | MeCN | 2% | 20 |
| 3 | Toluene | 2% | 59 |

[a]The average product yield from three independent experiments

TABLE 10

Base screening.

| Entry | Base | Yield (%) |
|---|---|---|
| 1 | Quinuclidine | 95 ± 1[a] |
| 2 | DABCO | 77 |
| 3 | DABCO, 36 h | 97 |
| 4 | DBU | 9.0 |

TABLE 10-continued

Base screening.

| Entry | Base | Yield (%) |
|---|---|---|
| 5 | $K_2CO_3$ | 0 |
| 6 | $KH_2PO_4$ | 0 |
| 7 | $K_3PO_4$ | 0 |
| 8 | 10% quinuclidine + 1 equiv $K_2CO_3$ | 0.33 (trace) |

[a] The average product yield from three independent experiments

TABLE 11

Alcohol scope.[a]

| Entry | Alcohol | Yield (%) |
|---|---|---|
| 1 | MeOH | 95 ± 1[b] |
| 2 | 1-hexanol | 90 |
| 3 | Benzyl alcohol | 86 |

[a] General reaction condition (1M in THF, Ni catalyst 2 wt %) was used
[b] The average product yield from three independent experiments

TABLE 12

Ni catalyst.[a]

| Entry | Ni source | Yield (%) |
|---|---|---|
| 1 | $(^{Me}N3)NiCl_2$ | 95 ± 1[b] |
| 2 | $(^{Me}N3)NiBr_2$ | 90 |
| 3 | $(^{iPr}N3)NiCl_2$ | 82 |
| 4 | $^{Me}N3 + Ni(DME)Cl_2$ | 77 |
| 5 | $[(^{iPr}N3)Ni^{III}(PhAc)Br]PF_6$ | 31 |

[a] General reaction condition (1M in THF, Ni catalyst 2 wt %) was used
[b] The average product yield from three independent experiments

Example 5. Thermodynamic Feasibility Examination of Photocatalytic Process

TABLE 13

Redox Potentials of Photocatalyst, Nickel complexes and Quinuclidine.[a]

| Compounds | Reductive Quenching | | Oxidative Quenching | | Product yield (%) |
|---|---|---|---|---|---|
| | *M/M$^-$ (V) | M/M$^-$ (V) | M$^+$/*M (V) | M$^+$/M (V) | |
| $[Ru(bpz)_3](PF_6)_2$ | 1.45 | −0.80 | −0.26 | 1.86 | 0 |
| $[Ru(phen)_3]Cl_2$ | 0.82 | −1.36 | −0.87 | 1.26 | 0.9 (trace) |
| $[Ir(ppy)_2(dtbbpy)]PF_6$ | 0.66 | −1.51 | −0.96 | 1.21 | 98 |
| fac-Ir(ppy)$_3$ | 0.31 | −2.19 | −1.73 | 0.77 | 90 |
| $[Ir(dF(CF_3)_2ppy)(dtbbpy)]PF_6$ | 1.21 | −1.37 | −0.89 | 1.69 | 86 |
| $(^{iPr}N3)NiCl_2$ (1 b) Ni$^{III/II}$ | | −0.82[b] | | | |
| $(^{iPr}N3)NiCl_2$ (1 b) Ni$^{III/II}$ | | | | 1.11 | |
| $(^{iPr}N3)Ni(PhAc)Br$ (4) Ni$^{III/II}$ | | | | 0.06 | |
| Quinuclidine$^{•+}$/Q | | | | 1.09 | |

[a] All redox and excited-state redox potential were corrected from known experimental values using conversion constants for redox potentials, and reported vs SCE.
[b] irreversibility of the peak prevents accurate assignment of the redox potential.

Based on photoredox/Ni dual catalysis with blue LED experiment results, we evaluated thermodynamic feasibility of photocatalysts in the C—O coupling reaction for additional mechanistic insight (Table 13). Regarding photoredox/Ni dual catalysis, two distinct mechanisms can be considered: a reductive quenching or an oxidative quenching mechanism.

First of all, the mechanism composed of photocatalyst reductive quenching M/*M/M$^-$/M cycle and Ni$^0$/Ni$^{II}$/Ni$^{III}$/Ni$^I$/Ni$^0$ cycle has been considered. In our results, both of strong oxidant $[Ir(dF(CF_3)_2ppy)(dtbbpy)]PF_6$ (E(*Ir$^{III}$/Ir$^{II}$)=+1.21 V vs SCE) and weak oxidant fac-Ir(ppy)$_3$ (E(*Ir$^{III}$/Ir$^{II}$)=+0.31 V vs SCE) successfully generated the desire C—O coupled product. In this scenario, the Ni$^{II}$ species involved as a catalytic intermediate would be ($^R$N3)Ni$^{II}$Ar(OR), as proposed by MacMillan et al (Nature 2015, 524, 330). Considering redox potentials of Ni complexes and photocatalysts (Ir and Ru complexes), it implies that the reductive quenching pathway involving $[Ru(phen)_3]Cl_2$ (E(*Ru$^{II}$/Ru$^I$)=+0.82 V vs SCE) is also thermodynamically feasible, and therefore could mediate the reaction. However, only a trace amount of product was observed with $[Ru(phen)_3]Cl_2$, and the observed production yields contradicts the trend of oxidation strength of excited photocatalysts ($[Ir(dF(CF_3)_2ppy)(dtbbpy)]PF_6$>$[Ru(phen)_3]Cl_2$>fac-Ir(ppy)$_3$).

Therefore, we propose that the reductive quenching cycle might not be operating in our system. The other possibility includes oxidative quenching of photocatalyst *M/M$^+$/M/*M cycle and Ni$^{II}$/Ni$^I$/Ni$^{III}$/Ni$^I$/Ni$^{II}$ cycle. In this case, the key step in the catalytic cycle is the single-electron reduction of Ni catalyst by the excited photocatalyst. As seen in our results, all the photocatalysts with excited state reduction potential E(M$^+$/*M)<−0.87 V successfully afforded a significant amount of C—O coupling product. Although our experimentally obtained redox potential of Ni$^{III/I}$ (−0.82 V vs SCE), which is slightly less negative than that of $[Ru(phen)_3]Cl_2$ (E(Ru$^{III}$/*Ru$^{II}$)=−0.87 V vs SCE), suggests SET process between Ni and *Ru is thermodynamically feasible, we believe that irreversibility of Ni$^{III/I}$ peak prevents correct assignment of the reduction potential and values are fall within the margin of error.

Taken together, we postulate the preferred mechanistic pathway may not involve a Ni$^{II}$ to Ni$^{III}$ oxidation by the excited photocatalyst, instead would be involving a SET Ni$^{II}$ to Ni$^I$ reduction process. We note that for some photocatalysts (such as fac-Ir(ppy)$_3$), regeneration of photocatalyst (M$^+$ to M) can also occur in concurrence with quinuclidine oxidation (estimated oxidation potential E$_p$=+1.09 V vs SCE).

Summary

This technology presents the novel synthetic approach of a new class of $^R$N3 ligands featuring a chemically robust macrocycle with a flexible chelating arm. Utilization of the N-nitroso reduction reaction in pyridinophane chemistry enables the design of more elaborate ligand structures, not readily accessible through known synthetic routes. The reaction precursor ($^{TsH}$N4) is a known chemical that can be easily synthesized by following our reported procedure. The N-nitroso reduction conditions are mild, suggesting a broad functional group tolerance. As all of the reaction steps toward the target molecules $^R$N3 are not requiring extensive purification steps, the yield of each step is fairly high. This discovery of this novel synthetic route would enable developing more diverse structures of ligands, by further functionalization or starting from different chemical precursors.

Unlike commonly used linear tridentate N3 type ligands, these new macrocyclic $^R$N3 ligands are fairly rigid to enforce facial capping coordination, while also containing a flexible arm that can control the reactivity of the metal center. As such, this unique $^R$N3 can be a useful ligand structure for a wide field of coordination chemistry. In addition, the use of N-donor ligands in which the pyridyl groups are perpendicular to the equatorial plane of the metal center have never been used in catalysis to date.

Synthesis of various transition metal complexes which would provide desired properties depends on the field of application. We are showing herein the synthesis of various Nickel complexes, for which results show they are very efficient catalysts for photoredox catalysis for the formation of C—C and C-heteroatom bonds.

In our preliminary study, we discovered that Ni complexes supported by newly developed ligand $^{Me}$N3 could successfully catalyze the cross-coupling reaction of 4-bromoacetophenone with methanol under irradiation with purple LED light in the absence of additional photocatalysts, or irradiation with blue LED light in the presence of additional photocatalysts. Visible-light photocatalysis or photoredox catalysis has recently received increasing attention from chemists due to its wide application in organic synthesis and its significance for sustainable chemistry, highlighting the mild reaction conditions by using convenient sources of light.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An organometallic compound of Formula I:

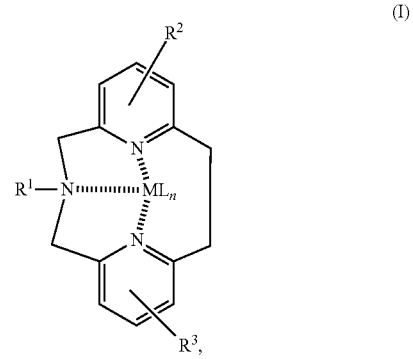

wherein

M is a transition metal;

L is a ligand and n is 1, 2, or 3;

$R_1$ is —($C_1$-$C_6$)alkyl, or —($C_3$-$C_6$)cycloalkyl; and $R^2$ and $R^3$ are each independently H, halo, —($C_1$-$C_6$)alkyl, —($C_3$-$C_6$)cycloalkyl, —O($C_1$-$C_6$)alkyl, or —N[($C_1$-$C_6$)alkyl]$_2$;

wherein each ($C_1$-$C_6$)alkyl moiety is independently unbranched or branched.

2. The compound of claim 1 wherein M is Ni, Cu, Co, Zn, Fe, Mn, Pd, Ru, or Rh.

3. The compound of claim 2 wherein M is Ni wherein Ni is Ni(II) or Ni(III).

4. The compound of claim 1 wherein L is halo, alkyl, aryl, nitrile, or a combination thereof when n is 2 or 3, wherein aryl is optionally substituted.

5. The compound of claim 1 wherein $R^1$ is methyl or isopropyl.

6. The compound of claim 1 wherein $R^2$ and $R^3$ are H.

7. The compound of claim 1 wherein the compound is:

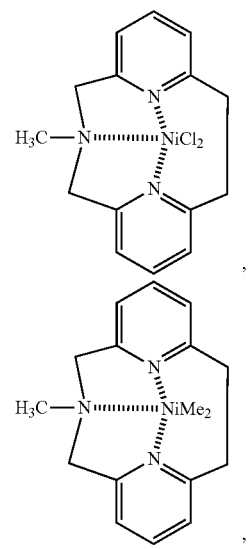

-continued

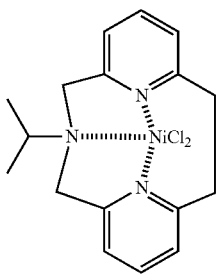

,

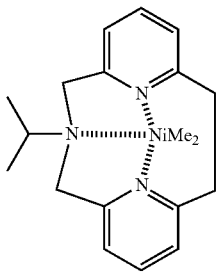

,

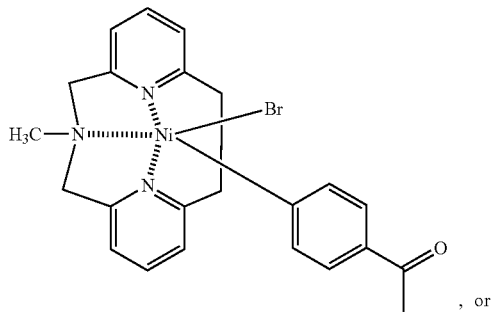

, or

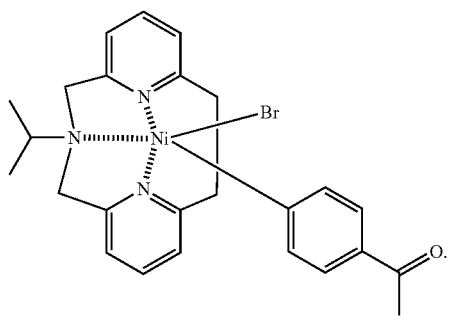

.

8. A macrocyclic compound of Formula II:

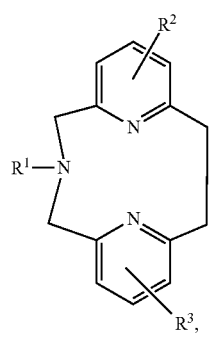

(II)

wherein

R$^1$ is —(C$_1$-C$_6$)alkyl, —(C$_3$-C$_6$)cycloalkyl, or arylsulfonyl; and

R$^2$ and R$^3$ are each independently H, halo, —(C$_1$-C$_6$)alkyl, —(C$_3$-C$_6$)cycloalkyl, —O(C$_1$-C$_6$)alkyl, or —N[(C$_1$-C$_6$)alkyl]$_2$;

wherein each (C$_1$-C$_6$)alkyl moiety is independently unbranched or branched.

9. The compound of claim 8 wherein R$^1$ is methyl, isopropyl, or para-toluenesulfonyl.

10. The compound of claim 8 wherein R$^2$ and R$^3$ are H.

11. The compound of claim 8 wherein the compound is:

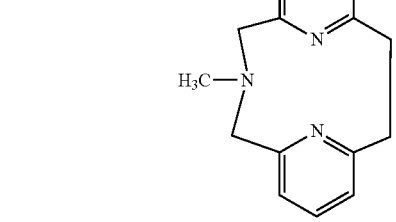

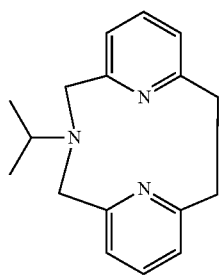

, or

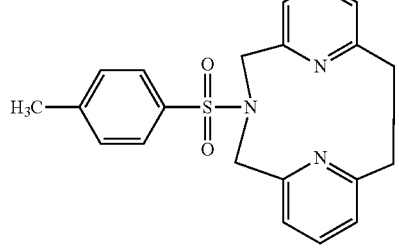

.

12. A composition comprising a compound of claim 8 and a suitable solvent.

13. The composition of claim 12 wherein the compound is:

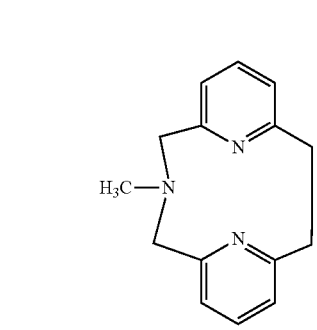

,

-continued

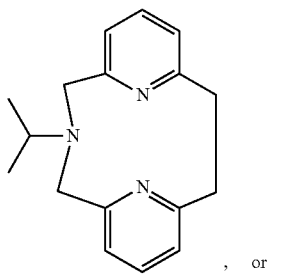

, or

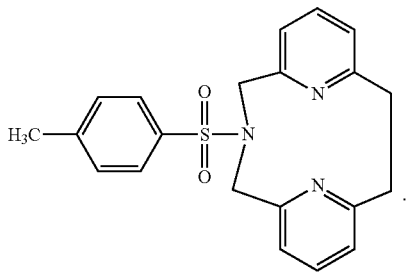

14. A method for preparing a pyridinophane comprising:

a) contacting a compound of Formula III:

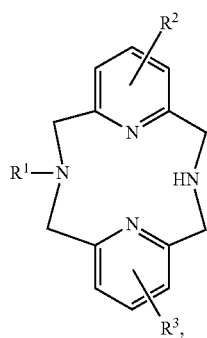

(III)

wherein

R¹ is a nitrogen protecting group; and

R² and R³ are each independently H, halo, —($C_1$-$C_6$) alkyl, —($C_3$-$C_6$)cycloalkyl, —O($C_1$-$C_6$)alkyl, or —N[($C_1$-$C_6$)alkyl]$_2$; wherein each ($C_1$-$C_6$)alkyl moiety is independently unbranched or branched;

and nitrous acid to form a nitrosamine; and b) reducing the nitrosamine under suitable reaction conditions to form a pyridinophane of Formula IIB:

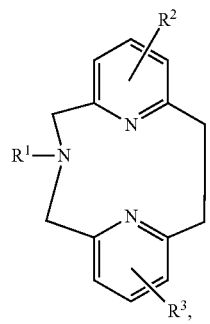

(IIB)

wherein R¹, R², and R³ is defined for Formula III.

15. The method of claim 14 wherein R¹ of the pyridinophane is para-toluenesulfonyl.

16. The method of claim 14 wherein the method further comprises:

c) removing the nitrogen protecting group from the pyridinophane of Formula IIB to form a secondary amine wherein R¹ is H;

d) alkylating the secondary amine to form a tertiary amine wherein R¹ is —($C_1$-$C_6$)alkyl;

e) contacting the tertiary amine and a transition metal salt to form a transition metal complex of the pyridinophane having one or more ligands; and f) optionally replacing ligands on the transition metal moiety of the complex with different ligands under suitable reaction conditions.

17. A method for cross-coupling comprising:

a) contacting an alcohol, a halo or sulfonate substituted aromatic compound, a catalytic amount of an organometallic compound of claim 1, and a base to form a mixture; and b) irradiating the mixture under suitable reaction conditions to cross-couple the alcohol and substituted aromatic to form a carbon-oxygen bond.

18. The method of claim 17 wherein the organometallic compound is:

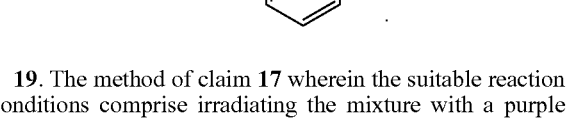

19. The method of claim 17 wherein the suitable reaction conditions comprise irradiating the mixture with a purple light emitting diode (LED).

20. The method of claim 19 wherein the LED emits light at a wavelength of about 390 nm.

* * * * *